United States Patent [19]

Buechel et al.

[11] 4,340,978
[45] Jul. 27, 1982

[54] NEW JERSEY MENISCAL BEARING KNEE REPLACEMENT

[75] Inventors: Frederick F. Buechel; Michael J. Pappas, both of Irvington, N.J.

[73] Assignee: Biomedical Engineering Corp., Newark, N.J.

[21] Appl. No.: 162,070

[22] Filed: Jun. 23, 1980

Related U.S. Application Data

[62] Division of Ser. No. 53,694, Jul. 2, 1979, Pat. No. 4,309,778.

[51] Int. Cl.³ .............................................. A61F 1/03
[52] U.S. Cl. .................................. 3/1.911; 128/92 C
[58] Field of Search ................................ 3/1.9–1.913; 128/92 C, 92 CA

[56] References Cited

U.S. PATENT DOCUMENTS

| | | |
|---|---|---|
| 3,869,731 | 3/1975 | Waugh et al. ........................ 3/1.911 |
| 3,964,106 | 6/1976 | Hutter, Jr. et al. ................. 3/1.911 |
| 4,081,866 | 4/1978 | Upshaw et al. ..................... 3/1.911 |
| 4,085,466 | 4/1978 | Goodfellow et al. ............ 3/1.911 X |
| 4,094,017 | 6/1978 | Matthews et al. .................. 3/1.911 |
| 4,224,696 | 9/1980 | Murray et al. ...................... 3/1.911 |

Primary Examiner—Clifford D. Crowder
Attorney, Agent, or Firm—Carella, Bain, Gilfillan & Rhodes

[57] ABSTRACT

A prosthesis for the surgical replacement of a dysfunctional knee joint is disclosed. The prosthesis includes a tibial platform, one or two tibial bearing inserts, and a femoral component.

In a unicompartmental embodiment of the invention, the tibial platform includes a spike for securing the tibial platform to the tibia. The tibial platform, in the unicompartmental embodiment, includes a track, which may be curved, and which is slidably engaged in dovetail fashion by a tibial bearing insert, typically of high molecular weight polyethylene. The superior surface of the tibial bearing insert is concave spherical, designed to slidably engage the inferior surface of the femoral component. The inferior surface of the femoral component is generally convex spherical, with radius of curvature slightly smaller than the radius of curvature of the tibial bearing insert. In some embodiments the inferior surface of the femoral component may have two or more differing radii of curvature at different points on such surface. Typically the tibial platform and the femoral component are constructed of cobalt-chromium alloy.

In a bicompartmental or tricompartmental embodiment of the invention, the tibial platform includes two tracks, each of which may be curved, and each of which slidably engages in dovetail fashion a tibial bearing insert. The two tibial bearing inserts each engage, via their superior concave spherical surfaces, mating inferior convex surfaces of the femoral component. The two curved tracks are in general not concentric; rather, the center of each falls on a line normal to the plane of such curved track and passing through the center of curvature of the concave spherical surface of the tibial bearing insert of the other curved track.

6 Claims, 76 Drawing Figures

FIG. IA
FIG. IB
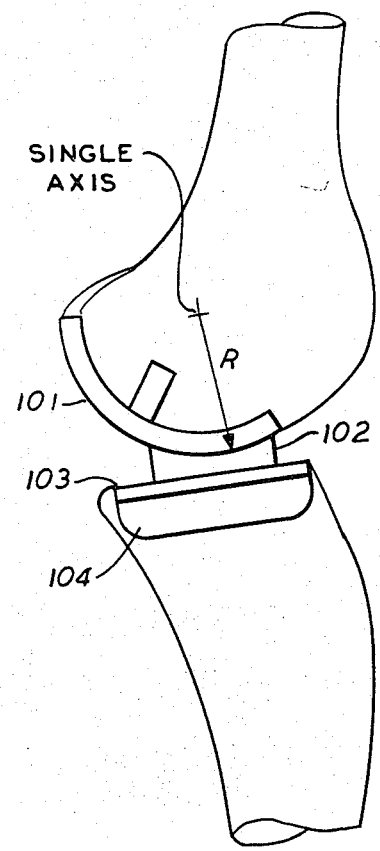
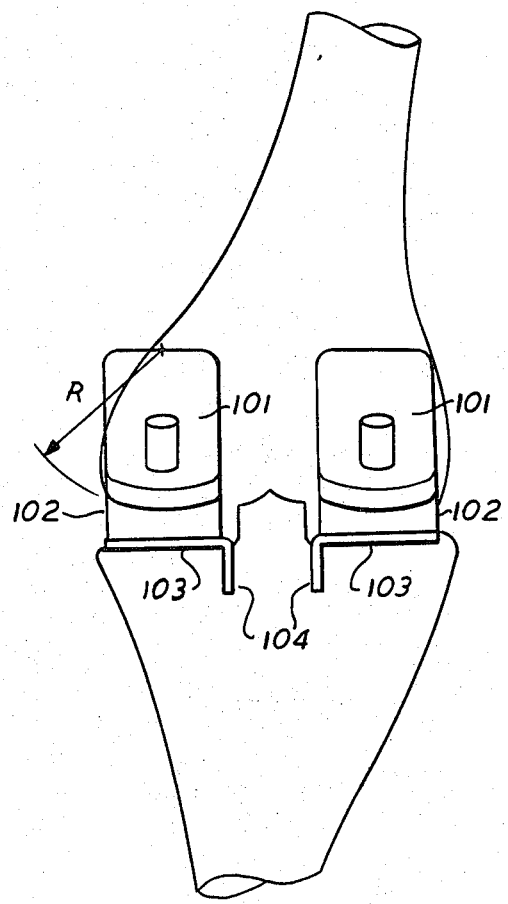
FIG. 3A
POSITION OF BEARING INSERTS AT 90° FLEXION WITH NO ROTATION
FIG. 3B
POSITION OF BEARING INSERTS AT 90 FLEXION WITH 15° AN 30° AXIAL ROTATION
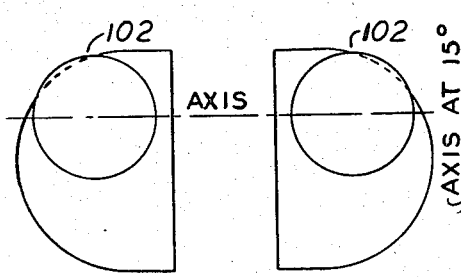
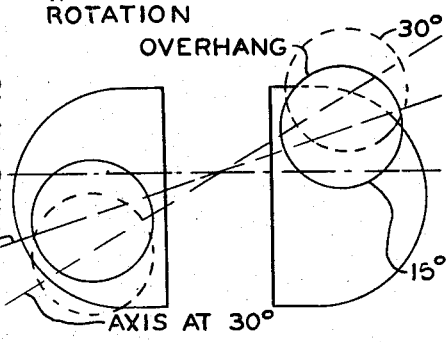

85° FLEXION

120° FLEXION

SWING PHASE OF WALKING

KNEE DISTRACTED INSERT FREE TO DISLOCATE

HIGH STRESS DUE TO HIGHLY INCONGRUENT CONTACT

HIGH COMPRESSION STRESS

LIMIT OF TRAVEL

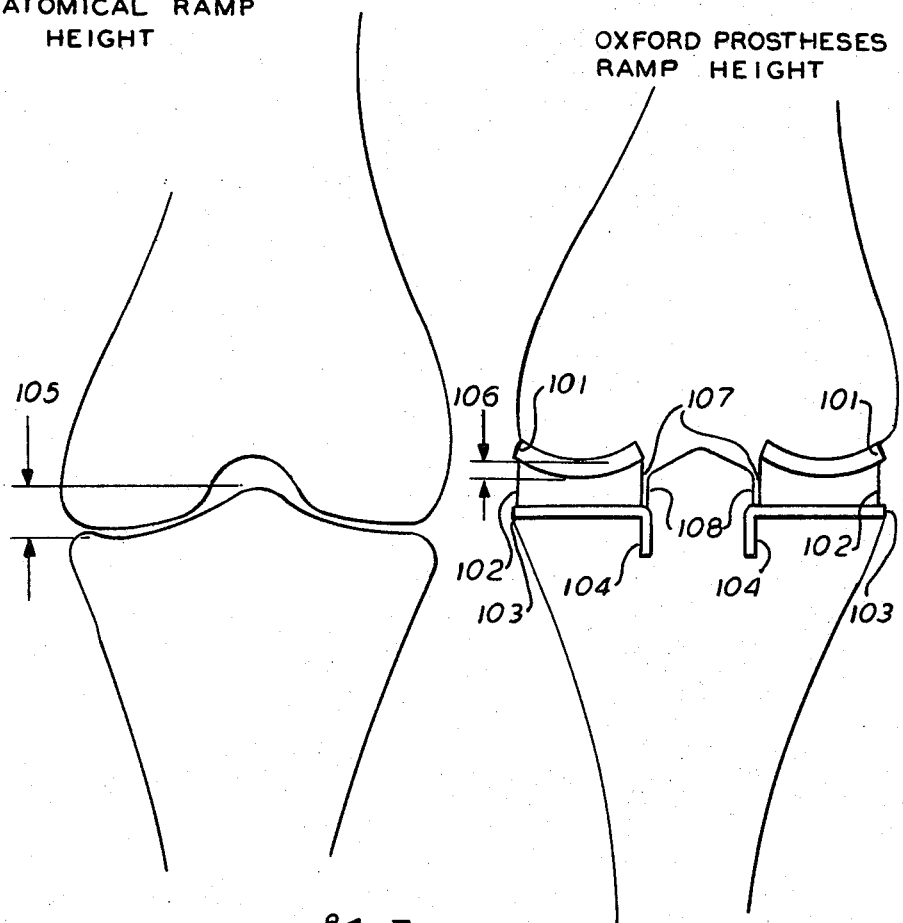
FIG. 5A
ANATOMICAL RAMP HEIGHT
FIG. 5B
OXFORD PROSTHESES RAMP HEIGHT
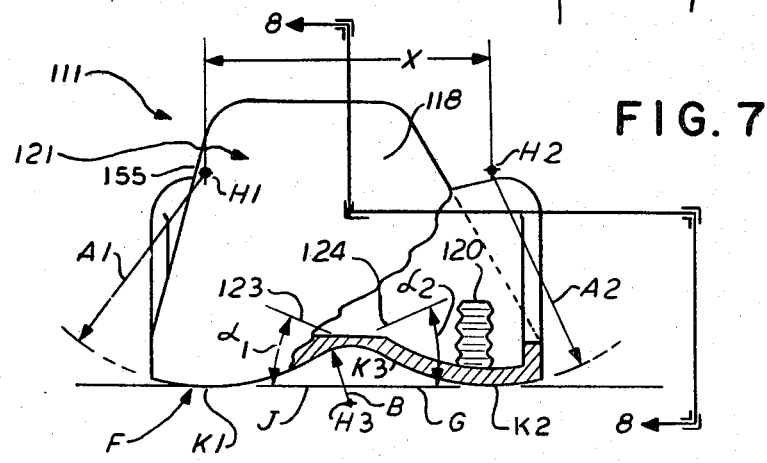
FIG. 7

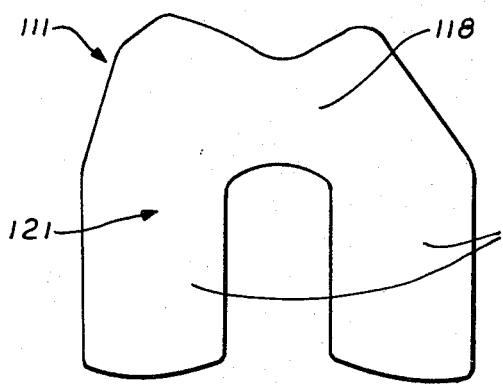
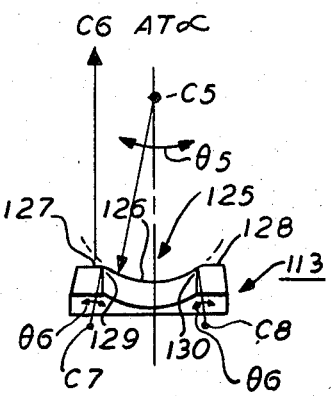
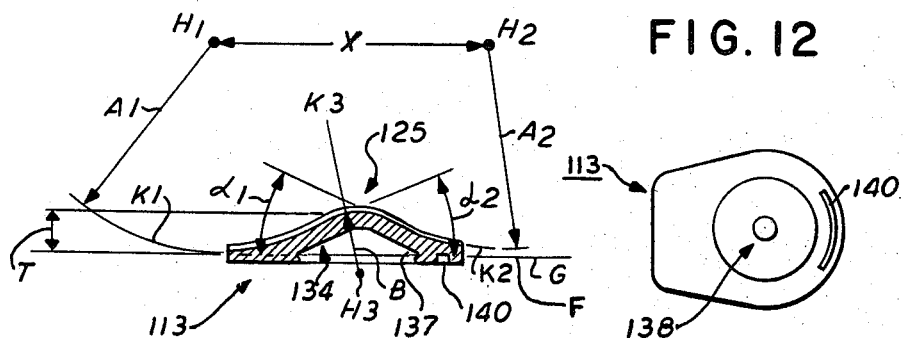
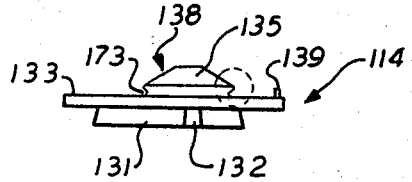
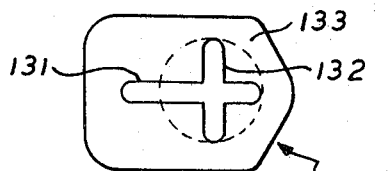
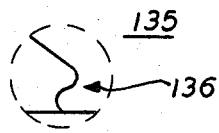

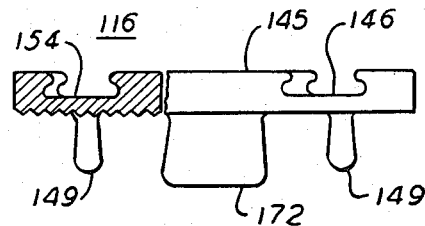
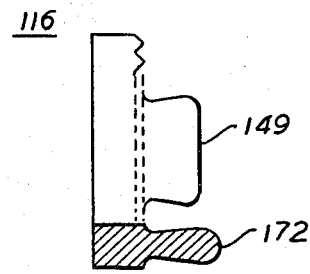
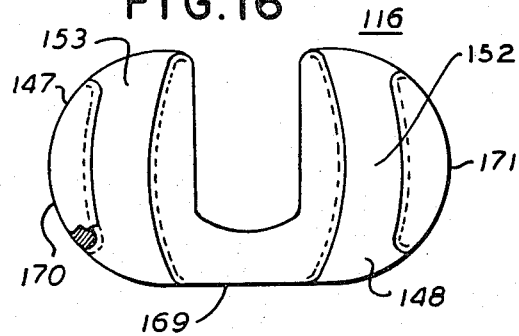
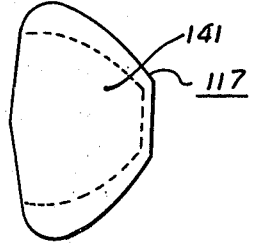
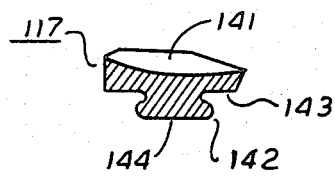
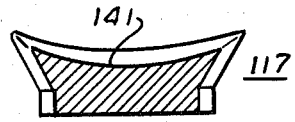
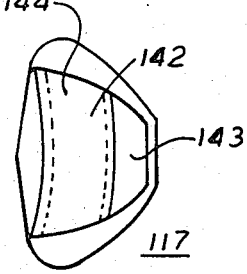
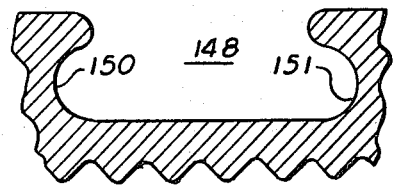

FIG. 24
FIG. 25
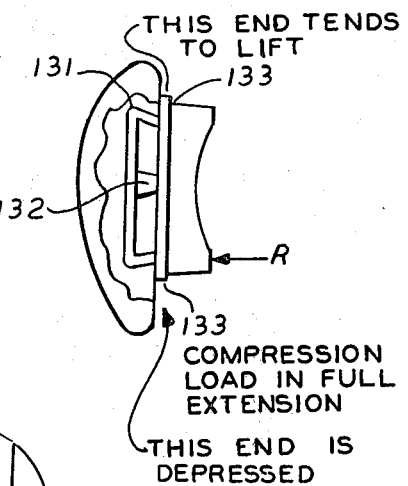
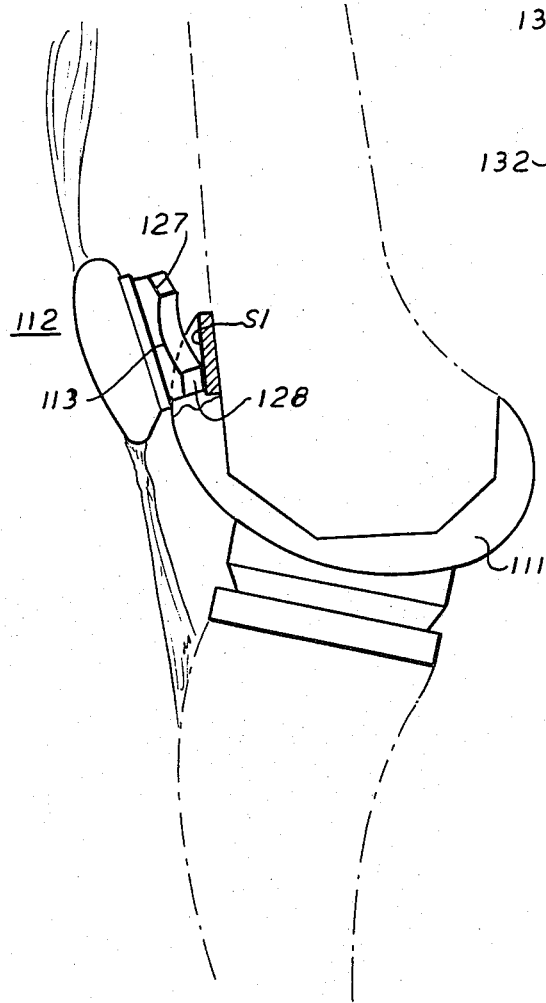

FEMORAL ANTERIOR ARTICULAR CARTILIGE FOR PATELLA-FEMORAL ARTICULATION

FEMORAL POSTERIOR ARTICULAR CARTILIGE FOR TIBIO-FEMORAL ARTICULATION

INTERIOR VIEW OF DISTAL FEMUR

LOW COMPRESSION FORCE

MODERATE COMPRESSION FORCE

FIG. 32A
FIG. 32B
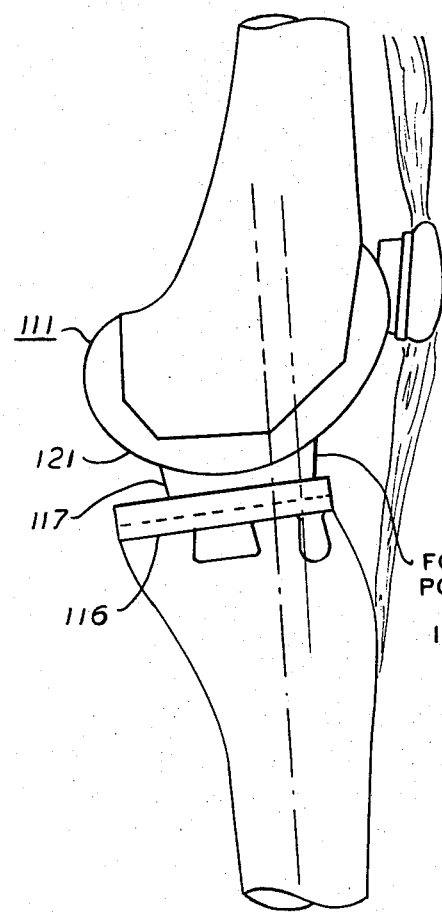
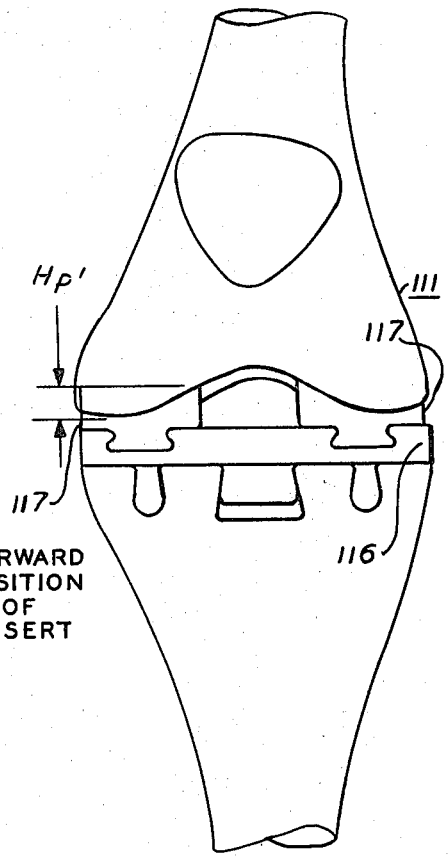
FIG. 36
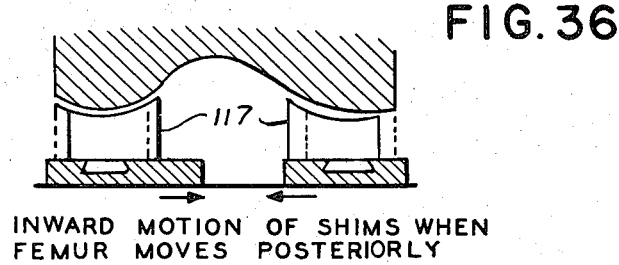
INWARD MOTION OF SHIMS WHEN FEMUR MOVES POSTERIORLY

15° FLEXION

KNEE IN FLEXION $H_{P1}$ SMALLER HEIGHT PROVIDES GREATER CENTER DISTANCE CHANGE FOR A GIVEN AMOUNT OF INCONGRUITY $H_{P2}$ LARGER HEIGHT PROVIDES GREATER MEDIAL-LATERAL STABILITY

OUTWARD SHIFT
ALLOWABLE INWARD SHIFT

NJ CENTERING VECTOR
OXFORD CENTERING VECTOR

TENDS TO LIFT ANTERIOR ASPECT OF PROSTHESIS-FIN PROVIDES POOR TENSION RESISTANCE
164
TENSILE STRESS
166
HIGH COMPRESSION STRESS

PROSTHESIS TENDS TO LIFT ON MEDIAL BORDER AND SPREAD THE BONE FIN PROVIDES LITTLE TENSION RESISTANCE
165
166
POTENTIAL FRACTURE
STRESS CONCENTRATION AT BOTTOM OF SLOT COUPLED WITH SPREADING EFFECT OF FIN BLADE 167
168

167
168

FIG. 45
FIG. 46
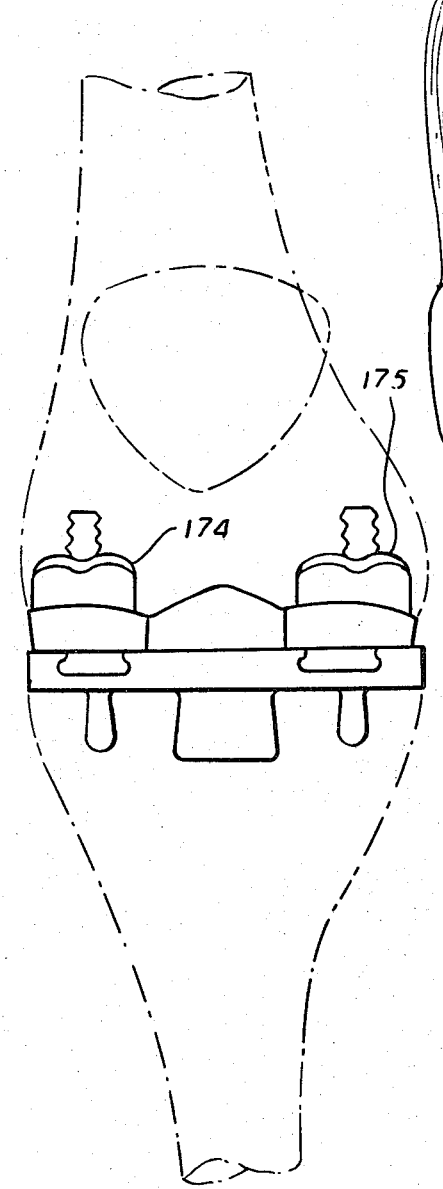
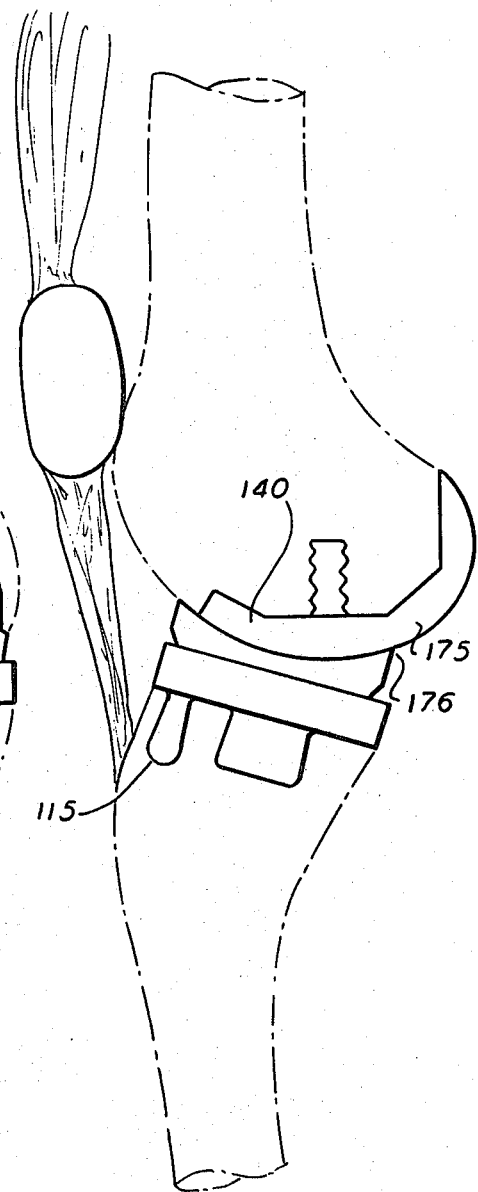

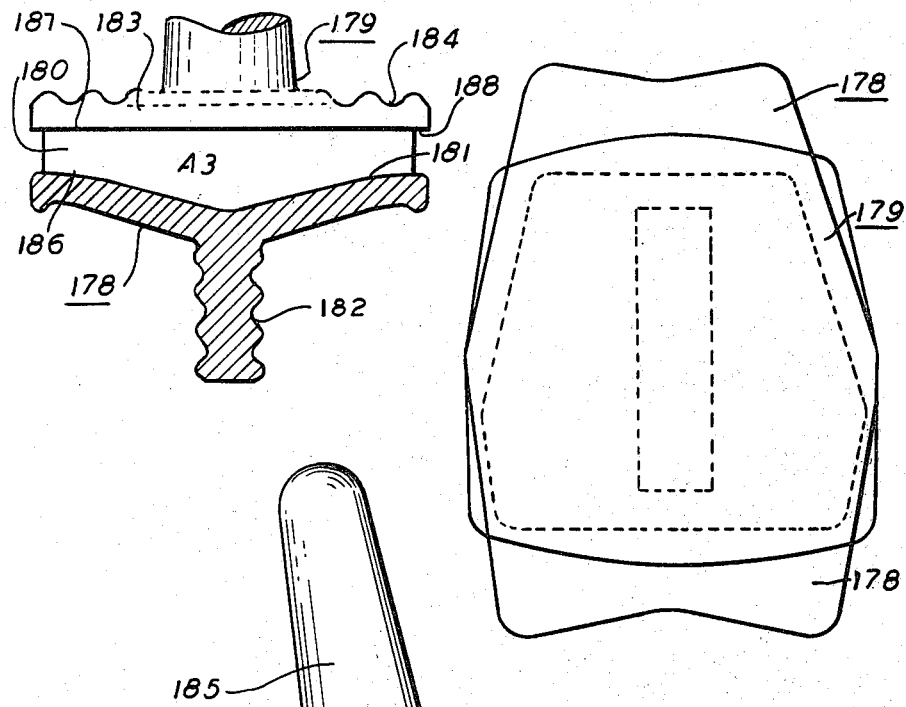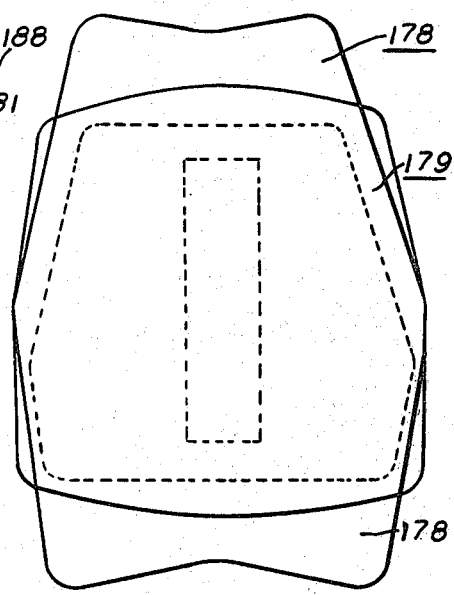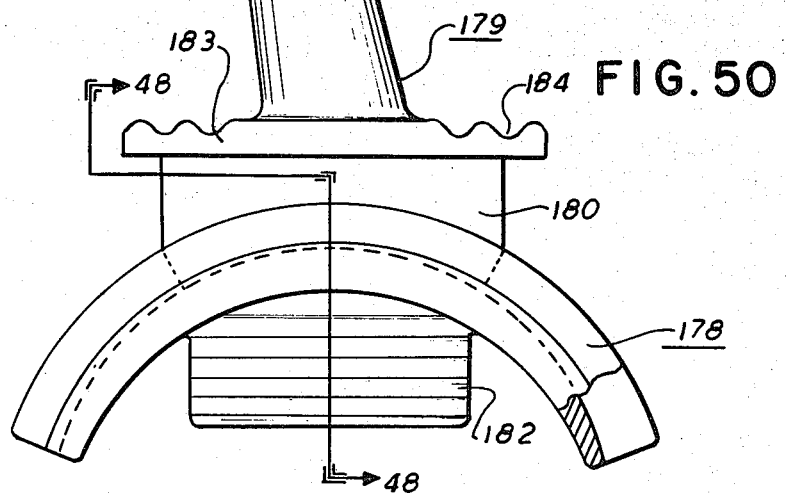

NEW JERSEY MENISCAL BEARING KNEE REPLACEMENT

This is a division, of application Ser. No. 53,694 filed July 2, 1979, now U.S. Pat. No. 4,309,778.

TECHNICAL FIELD

This invention relates to prosthetic joints generally, and more particularly to a prosthesis for replacement of a dysfunctional knee joint.

BACKGROUND ART

Referring now to prior art knee endoprostheses, and in particular to the prior art knee prostheses with patello-femoral replacement, it has been observed that such prior art prostheses have poorly designed patello-femoral interfaces in that they do not provide reasonable congruent patello-femoral contact or sliding engagement over any appreciable range of knee motion.

More particularly, such prior art prostheses typically produce contact stresses which result in yielding and fatigue of the plastic bearing surface typically present in such prostheses. This result is caused by the fact that the bearing surface of the femoral component, over which the patella prosthesis must pass, generally has several regions or segments of differing shape. For example, there is typically a fairly long, singly curved segment blending into a first doubly curved segment blending again into a second, and different, doubly curved segment. These varying segments or regions provide the femoral portion of the femoral-tibial articulation, and those segments or regions do not have a common generating curve. Thus, when the patella prosthesis goes through its excursion over the femoral articular flange, the patella prosthesis undergoes a variety of contact conditions, namely, substantial portions of line contact, portions of point contact, and perhaps limited portions of area or congruent area contact. As is known, line contact and point contact conditions generally produce high contact stresses which produce yielding and substantial wear of plastic prostheses. Hence, the extended wear life needed for successful prosthetic implantation is not realized.

Referring next to typical prior art tibio-femoral knee prostheses, it has been observed that those prior art knee prostheses which allow axial rotation and anterior-posterior motion in addition to flexion-extension motion have incongruent contact (usually theoretical point-contact) between the femoral and tibial bearing surfaces, producing excessive contact stresses leading to deformation and/or early wear and undesirably short prosthetic life. Also, wear products have been shown to produce undesirable tissue reactions which may contribute to loosening of the prosthetic components.

Those prior art knee prostheses which do provide congruent or area bearing contact fail to provide the needed axial rotation, or when cruciates are present the needed anterior-posterior motion. This lack of axial rotation and anterior-posterior motion has been shown clinically and experimentally to result in deformation and loosening of the tibial components, and such prostheses now appear to be falling into disuse.

Current prostheses of the dislocatable cruciate retaining type, such as the Geomedic knee replacement shown in U.S. Pat. No. 3,728,742 issued Apr. 24, 1973 to Averill et al., that produce area contact provide only one axis of rotation relative to the femur for the flexion-extension motion. Normal flexion-extension is, however, characterized by a polycentric flexion-extension motion where rotation relative to the femur occurs about many axes. This polycentric motion, which results from the action of the cruciate ligaments and condylar shape, allows for more efficient utilization of muscle forces by providing a posterior shift of the axis when effective quadriceps action is important and an anterior shift when hamstrings effectiveness is important. Furthermore, in the human knee it is this polycentric action, and the shape of the posterior condyles, which influence this motion so as to allow full flexion capability for the knee. Failure to provide appropriate knee geometry inhibits, when cruciate ligaments are present, this natural polycentric motion and thus tends to restrict muscle effectiveness and inhibit flexion. These restrictions tend to increase both loading on the prosthesis (which increases wear or likelihood of deformation or breakage) and loading between prosthesis and bone (which increases the possibility of component loosening).

Other knee designs, such as the Townly type, avoid overconstraint by introducing incongruency of the articulating surfaces. The incongruency, while necessery to avoid overconstraint, unfortunately results in instability and excessive contact stresses.

It is further believed that loosening problems result from the direct attachment of plastic prosthetic components to bone through the use of relatively brittle cement that is weak in tension. Specifically, it has been demonstrated that even relatively thick plastic components when loaded in a normal fashion produce undesirable tensile stresses in the acrylic cement commonly used to secure such plastic components to bone. Such loading tends to produce bending of the plastic component which causes the ends of the plastic component to lift away from the bone, thereby subjecting the bone-cement attachment to tension. As is known, cement has very poor tensile fatigue properties. The bone to which the plastic prosthesis is cemented also appears to be adversely affected by tensile loads. Accordingly, it is believed that these combined effects contribute substantially to prosthetic loosening problems and, specifically, it has been noted where clinical failure due to loosening occurs in a knee prosthesis that it is almost always the plastic prosthesis component which loosens.

Another prior art prosthesis problem exists with regard to knee endoprostheses for implantation in those cases wherein the cruciate ligaments are functionally absent but where the collateral ligaments are functional or at least reconstructable. In the absence of cruciate ligaments, the prosthetic replacement must provide anterior-posterior knee joint stability so as to replace that stability otherwise provided by the cruciates. Until recently most such cases were treated by a stable hinge-type knee prosthesis which, unfortunately, appears to suffer from the loosening problems described above and furthermore typically produces substantial bone loss as a result of the relatively great bone resection required for implantation. Necrosis of the bone, caused by altered mechanical bone stresses, is also a problem with the hinge-type knee prostheses. More recent attempts have been made to treat such cases with surface replacement prostheses such as the prostheses known as the Total Condylar and similar knee prostheses. However, these knee prostheses have theoretical point-contact bearing surfaces with their above-noted attendant problems and, in addition, such prostheses tend to have instability and dislocation problems which result, at least in part, from these point-contact bearing surfaces.

Where the cruciate ligaments are present, most surgeons would prefer their retention, since they provide important internal stabilizers and, together with the condylar geometry of the femur and tibia, control the rotation axis of the knee. Furthermore, these ligaments provide anterior-posterior (A-P) stability. Thus, it is desirable to reserve the cruciate ligaments, even though reasonable stability can be provided by a properly designed full platform type prosthesis.

In addition, the action of the cruciate ligaments produces a shift in the rotation axis of the knee which may result in more efficient muscle utilization. Thus, preservation of these structures may provide better physiological function after knee replacement.

Still, it is not clear that the physiological advantages gained in retaining the cruciates outweigh the disadvantages of the design compromises, such as increased bearing surface incongruency and reduced tibial prosthesis bearing area, required to retain these ligaments. Thus, the desirability of retaining the cruciate ligaments in the cases of bicompartmental and tricompartmental replacement is not well established. The design described herein, however, eliminates or compensates for these design compromises, thus allowing the benefits of cruciate retention with minimal or no apparent loss in the abiliy of the prosthesis to withstand the loads to which it is subjected.

In unicompartmental replacement, the cruciates must be retained in any event since there is insufficient stability in their absence with a unicondylar replacement. Thus, for such cases a design which accommodates the cruciate ligaments is necessary.

Unicompartmental replacement with a proper bearing design allows surgical restoration of a single diseased compartment, rather than the sacrifice of normal structures to replace all three compartments of the knee. Further, reducing the number of compartments replaced has the effect of reducing prosthesis wear products. Recent evidence strongly suggests that these wear products produce adverse physiological response to the prosthesis, including an increased tendency for the prosthesis to loosen from its boney attachment.

A recent experimental knee concept, the Oxford knee, appears to provide a partial solution to the problem of overconstraint while maintaining congruency by the use of meniscal floating elements. Unfortunately, this knee suffers from several design problems which appear to limit its usefulness. The present invention, the New Jersey Meniscal Bearing Knee Replacement (NJMBK) utilizes similar concepts in an improved fashion in order to avoid some of the anticipated difficulties of the Oxford design.

The Oxford knee is shown in FIGS. 1A and 1B. The femoral components 101 consist of two metal spherical segments, each of constant radius. Bearing inserts 102 are circular in shape with a shallow spherical superior surface and a flat inferior surface. The tibial onlays 103 consist essentially of two flat plates with fixation by means of a fin 104 at the medial edge of each such flat plate.

There are several serious problems with the design of the Oxford knee of FIGS. 1A and 1B. The most basic problem is the potential for dislocation of bearing inserts 102 resulting from the limited flexion range of the device. As can be seen from FIGS. 2A and 2B the design provides excellent congruent contact up to about 90° flexion. Beyond that point a surface of constant radius cannot provide proper contact within the geometric constraints imposed by having to fit the prosthesis to the human knee. Flexion substantially beyond 90° produces edge contact and resulting deformation and possible dislocation of bearing inserts 102. Although 90° of flexion is satisfactory from a functional standpoint, it is impractical to limit motion to this range, since activities will be encountered (such as sitting onto a low chair, or returning to the standing position after sitting in a low chair) where flexion substantially exceeds 90°.

The problem of insert dislocation is made more severe by axial rotation of the knee, as is shown in FIGS. 3A and 3B. In FIG. 3A, there is shown the position of bearing inserts 102 at 90° flexion, but with no axial rotation of the knee. In FIG. 3B there is shown the position of bearing inserts 102 at 90° flexion, but with 15° (solid lines) and 30° (dashed lines) of axial rotation as well. There is a pronounced overhang of bearing inserts 102, with resultant risk of dislocation, under the combination of 90° flexion and 30° axial rotation of the knee.

Normal distraction of one compartment of the knee during the swing phase of walking, as depicted in FIG. 4, also leaves bearing insert 102 of the prior-art Oxford knee free to dislocate.

A further disadvantage of the Oxford knee arises from the shallowness and placement of the arcs of the contact surfaces, as can be seen from FIGS. 5A and 5B. In FIG. 5A there is shown a normal knee joint, with the anatomical ramp height designated 105. Note, in FIG. 5B, that the Oxford prosthesis ramp height 106 is substantially less than the anatomical ramp height 105, and therefore the Oxford prosthesis provides less than normal medial-lateral stability. Thus, when medial-lateral shear loads are encountered, additional stress is placed on the cruciate ligaments, which may be already compromised by bone resection. Furthermore, such loading, in conjunction with flexion or extension, will produce undesirable rubbing between the edges 107 of bearing inserts 102 and the cut edges 108 of the tibial bone.

Other weaknesses of the Oxford design include lack of accommodation for patella replacement, and tibial plateau components with relatively poor load-bearing properties, as will be described later.

An alternate embodiment of the Oxford knee which attempts to deal with the problem of dislocation is depicted in FIGS. 6A–D. Unfortunately, this design has several deficiencies which make it unworkable, at least with materials now commonly used for such components. The anterior-posterior (A-P) travel limit is greatly restricted compared to that of the present invention. There is substantial unsupported area 109 of plastic bearing insert 102, as can be seen from the cross-sectional view of FIG. 6C. Flexure of the plastic bearing insert 102 will occur, transferring load to the remaining areas and thus greatly increasing bearing compressive stresses. High stress will occur in the inner cavity at the head of retaining pin 110, particularly at the edge of retaining pin 110 and at the contact between the end of retaining pin 110 and the inner cavity, as can be seen from the cross-sectional view of FIG. 6D. Furthermore, the use of retaining pin 110 makes installation of the bearing element difficult after implantation of femoral and tibial components, since it is necessary to separate the knee joint by stretching the ligaments an amount equal to the pin height in addition to the separation normally required to install bearing inserts 102.

SUMMARY OF THE INVENTION

The present invention is directed to an improved prosthesis for the replacement of all or a portion of a dysfunctional human knee joint.

An object of the present invention is to provide a knee prosthesis in which shift of the bearing insert with knee flexion is similar to the normal anatomical shift in the center of the area of contact between femoral and tibial condyles.

A further object of the present invention is to provide a knee prosthesis which facilitates rotation about one or more axes, even in the presence of perfect congruency and rigidity of the bearing surfaces.

A further object of the present invention is to provide a knee prosthesis with greater dislocation height, and hence improved dislocation characteristics, than are available with prior-art floating bearing insert type knee prostheses.

A further object of the present invention is to provide a knee prosthesis with improved medial-lateral stability, substantially unaffected by axial rotation or anterior-posterior (A-P) shift of the bearing insert or inserts.

A further object of the present invention is to provide a knee prosthesis which substantially reduces the possibility of tipping or dislocation of the bearing insert or inserts.

A further object of the present invention is to provide a knee prosthesis which allows full flexion of the reconstructed knee.

A further object of the present invention is to provide a knee prosthesis allowing retention of the cruciate ligaments and capable of both effective patello-femoral and tibio-femoral articulation.

A further object of the present invention is to provide a knee prosthesis having reduced tendency toward loosening and collapse, as compared with prior-art floating bearing insert type knee prostheses.

A further object of the present invention is to provide a knee prosthesis allowing retention of the cruciate ligaments in which contact stresses between the tibial platform and the tibia are minimized.

A further object of the present invention is to provide a knee prosthesis design which is adaptable to embodiments for unicompartmental, bicompartmental, and tricompartmental knee replacements.

BRIEF DESCRIPTION OF THE DRAWINGS

A complete understanding of the invention may be obtained from the detailed description which follows, together with the accompanying drawings, wherein:

FIGS. 1A and 1B are diagrammatic views of the prior-art Oxford knee.

FIGS. 3A and 3B also depict the prior-art Oxford knee. FIG. 3A shows, in plan view, the position of the bearing inserts at 90° flexion with no rotation of the knee. FIG. 3B shows the positions of the bearing inserts at 90° flexion in the presence of axial rotations of 15° and 30°.

FIGS. 5A and 5B compare the anatomical ramp height with the ramp height provided by the prior-art Oxford knee prosthesis.

FIGS. 7 through 9 show the femoral component of the present invention, the New Jersey Meniscal Insert Knee.

FIGS. 10 through 12 show the intermediate patella bearing component according to the present invention.

FIGS. 13 and 14 show the patella fixturing component according to the present invention.

FIGS. 15 through 17 show the tibial platform component according to the present invention.

FIGS. 18 through 21 show the intermediate tibial bearing component according to the present invention.

FIG. 24 shows the orientation of the patella prosthesis relative to the femoral component at full extension of the knee.

FIG. 25 illustrates the role of the fixturing fins (of the patalla fixturing component) in resisting tipping loads.

FIG. 26 shows the button portion of the patella fixturing component, which is used to retain the intermediate patella bearing component.

FIGS. 32A and 32B show the manner in which the intermediate tibial bearing components are held in a forward position, in the tibial platform, by virtue of the shape of the bearing surface of the femoral component.

FIG. 33A shows 15° flexion, while FIG. 33B shows 120° flexion.

FIG. 34 is a cross-sectional view of the curved track of the tibial platform component according to the present invention.

FIG. 36 illustrates the manner in which the intermediate tibial bearing components move slightly closer together as the femur moves posteriorly.

FIG. 38B illustrates the greater dislocation height of the present invention, and FIG. 38C illustrates the non-central spherical radius of the present invention.

FIGS. 45 and 46 show an implanted bicompartmental version of the present invention, utilizing a pair of individual femoral components.

FIGS. 48, 49 and 50 illustrate an ankle prosthesis according to the present invention. FIG. 48 is a cross-sectional view of the prosthesis, as indicated in FIG. 50.

DETAILED DESCRIPTION OF THE INVENTION

Figure 2A:
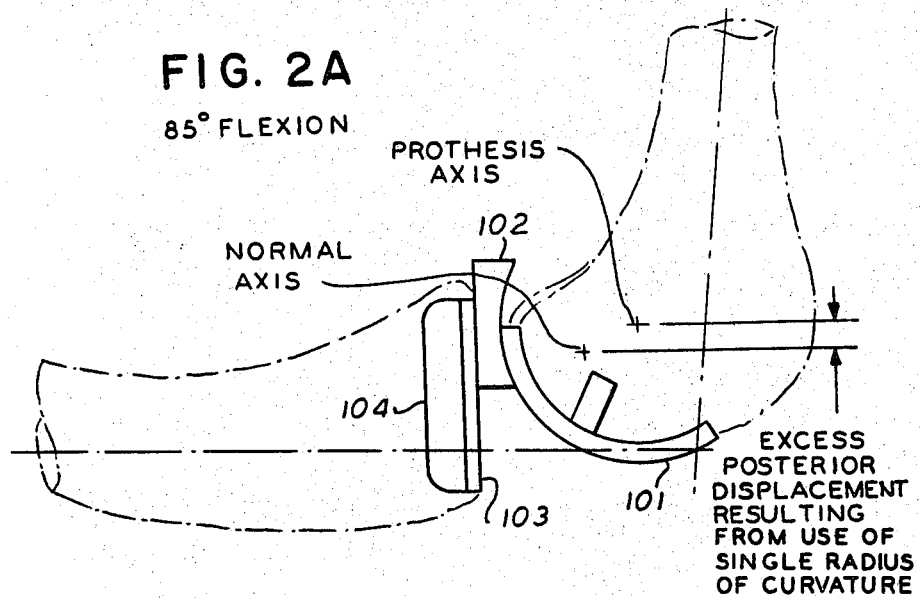
FIGS. 2A and 2B illustrate the prior-art Oxford knee at 85° and 120° (respectively) flexion, showing the excess posterior displacement of the bearing inserts at 85° flexion. Two possible dislocation modes of the bearing inserts are shown at 120° flexion.
Figure 2B:
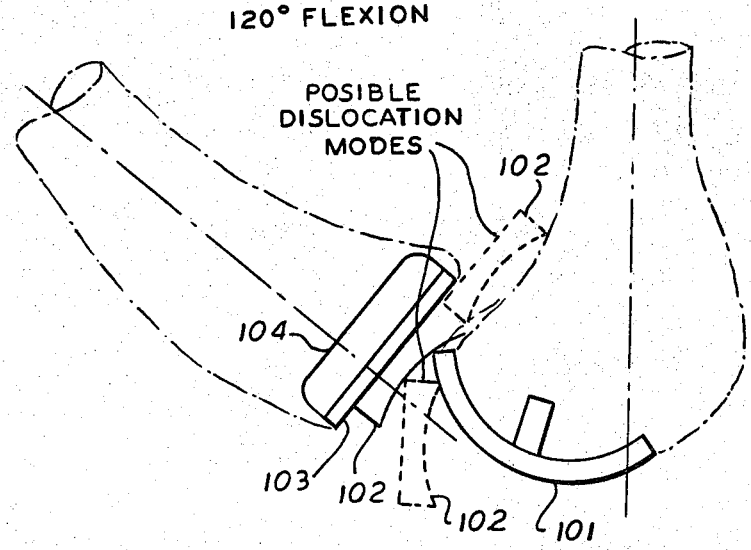
Figure 4:
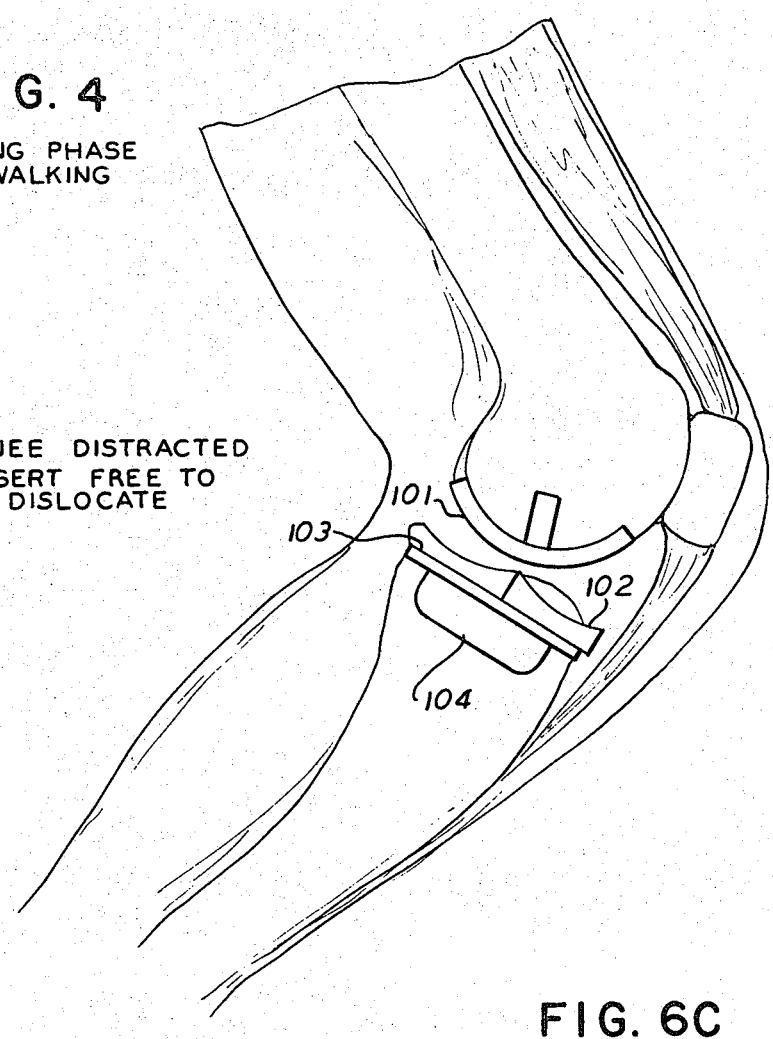
FIG. 4 illustrates the possibility of dislocation of the bearing inserts, in the prior-art Oxford knee, in the swing phase of walking.
Figure 6D:
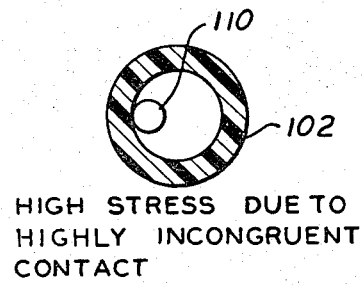
FIGS. 6A through 6D illustrate some of the disadvantages which result from a design modification to partially constrain the bearing inserts of the prior-art Oxford knee.
Figure 6C:
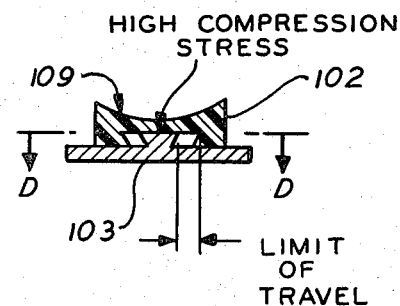
Figure 6A:
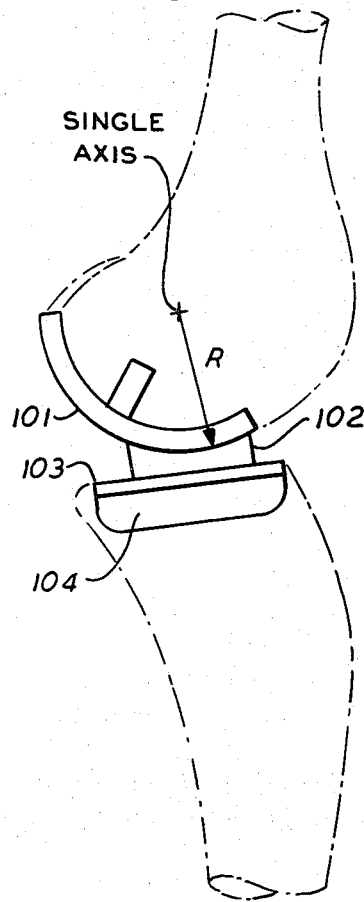
Figure 6B:
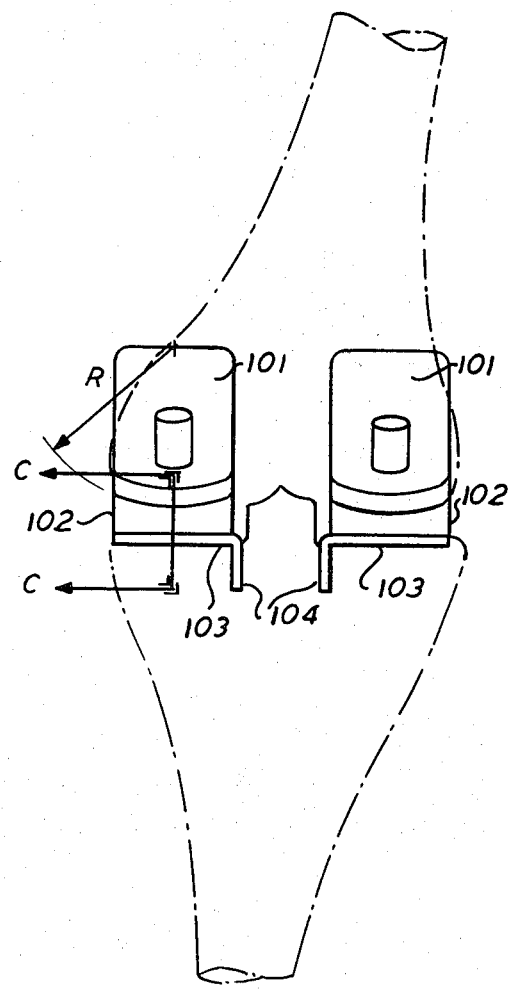
Figure 8:
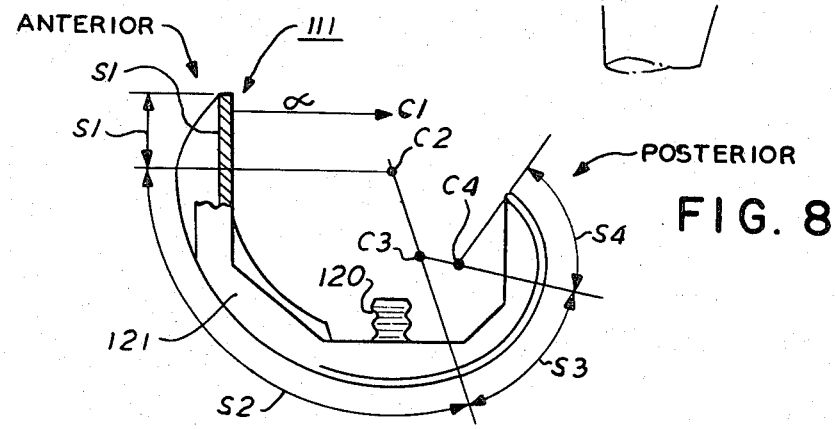
Figure 27:
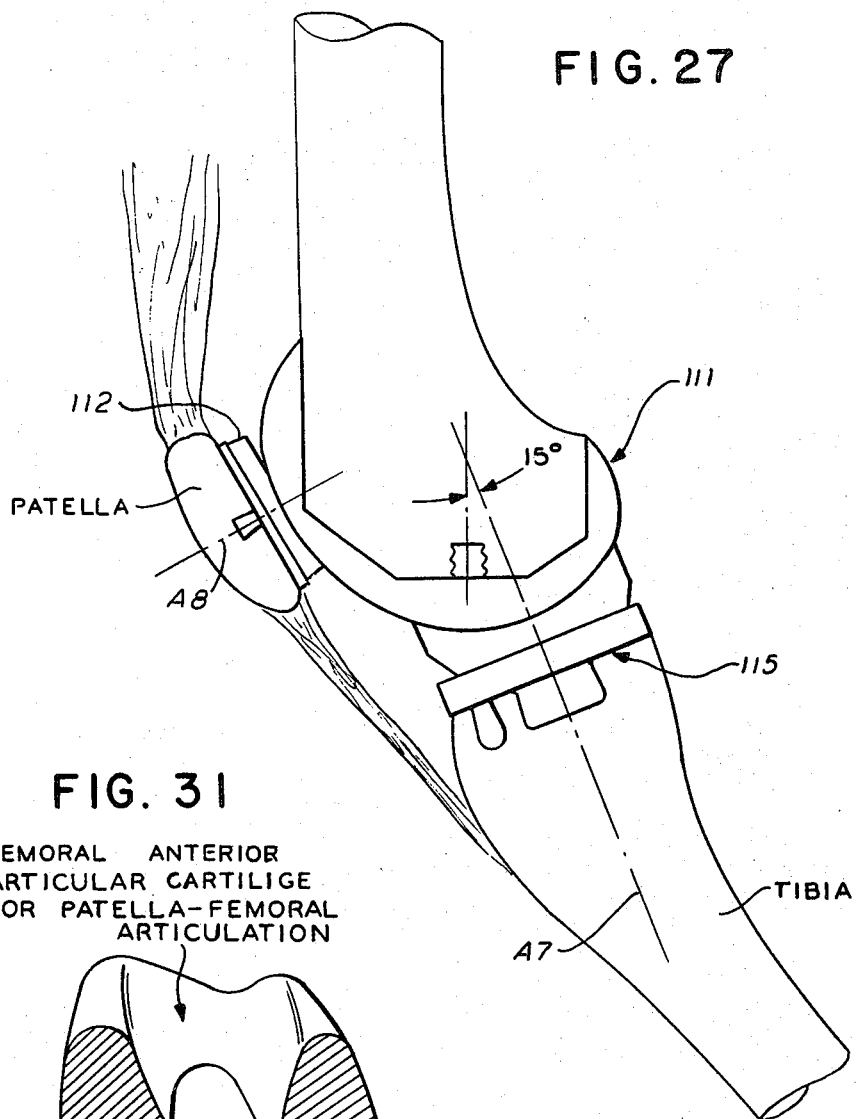
FIG. 27 shows the manner in which the present invention permits rotation of the patella with respect to the femoral bearing surface.

Referring now to FIGS. 7-21, there is shown an endoprosthesis embodying the present invention which has been referred to as a tricompartmental knee prosthesis and which includes the femoral component 111 best shown in FIGS. 7, 8, and 9; the patella prosthesis 112 shown in FIG. 27 and comprising the intermediate patella bearing component 113 best shown in FIGS. 10, 11, and 12, and the patella fixturing component 114 shown in FIGS. 13 and 14; and the tibial prosthesis 115 shown in FIG. 27 and comprising the tibial platform component 116 best shown in FIGS. 15, 16, and 17 and the intermediate tibial bearing components 117 shown in FIGS. 18, 19, 20, and 21.

Referring now to FIGS. 7, 8, and 9, there is shown in detail the femoral component 11 which includes, in the counter-clockwise anterior or posterior direction, a flange 118 formed integrally with two condyles 119—119. The femoral component 111 also includes a pair of fixturing posts; only one fixturing post, post 120, being shown. The outside surface of the flange 118 provides most of the bearing surface for patella articulation. The condyles 119 are provided for replacing the condylar surfaces of the human femur. The bearing surfaces of flange 118 and condyles 119—119 are referred to generally as the bearing surface 121. In accordance with the teaching of the present invention, bearing surface 121 in the counterclockwise anterior to posterior direction is a smooth, continuous surface formed by a series of segments of surfaces of revolution the respective shapes of which are generated or defined by rotating a common generating curve (generally identified as F) around a plurality of generating axes at respective pairs of major generating radii (or each at a respective major generating radius where the radii of each pair are equal) and through respective angles or rotation.

This common generating curve F is a smooth continuous plane curve and as may be understood from FIG. 7 the shape of which is defined by (i) two arcs K1 and K2 struck, respectively, by two radii A1 and A2 from respective centers H1 and H2 separated by a distance X; (ii) two tangent lines 123 and 124 respectively tangent to the arcs K1 and K2 and at angles $\alpha 1$ and $\alpha 2$, respectively, with respect to a line G tangent to arcs K1 and K2; and (iii) an arc K3 struck by radius B from center H3 and wherein arc K3 is also tangent to the tangent lines 123 and 124.

Figure 23:
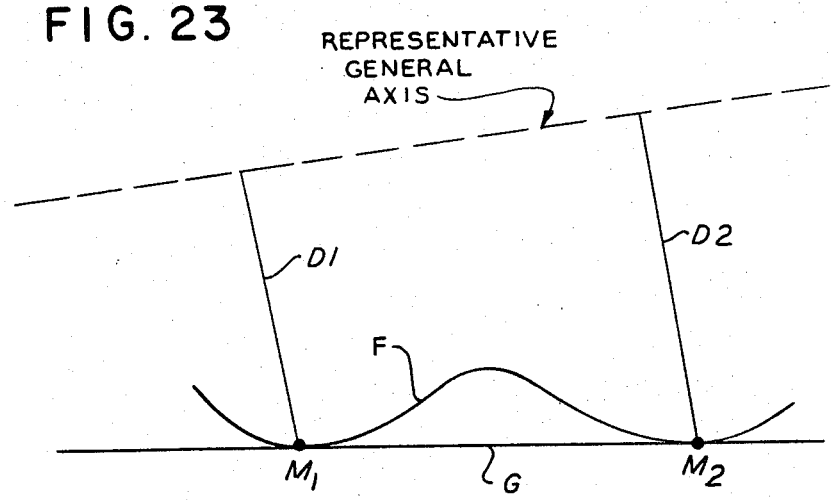
FIG. 23 illustrates the manner in which the several bearing surfaces of the present invention are generated by rotating a common generating curve about a particular generating axis at pairs of major generating radii.

Referring now to FIG. 23, where a further understanding of the general teachings of the present invention is illustrated, it will be understood that the shape of the bearing surface 121 (FIG. 7) is defined or generated by a series of segments of surfaces of revolution each of which segments is defined or generated by rotating the common generating curve F around a respective generating axis at respective pairs of major generating radii (or each at a major generating radius where the radii of each pair of major generating radii are equal) and through a respective angle of rotation. In generating each segment of a surface of revolution, the common generating curve F is oriented with respect to a generating axis by a pair of major generating radii D1 and D2 which are the respective distances (shortest distances) from points M1 and M2 where the common generating curve F contacts tangent line G as shown in FIG. 23.

Figure 22:
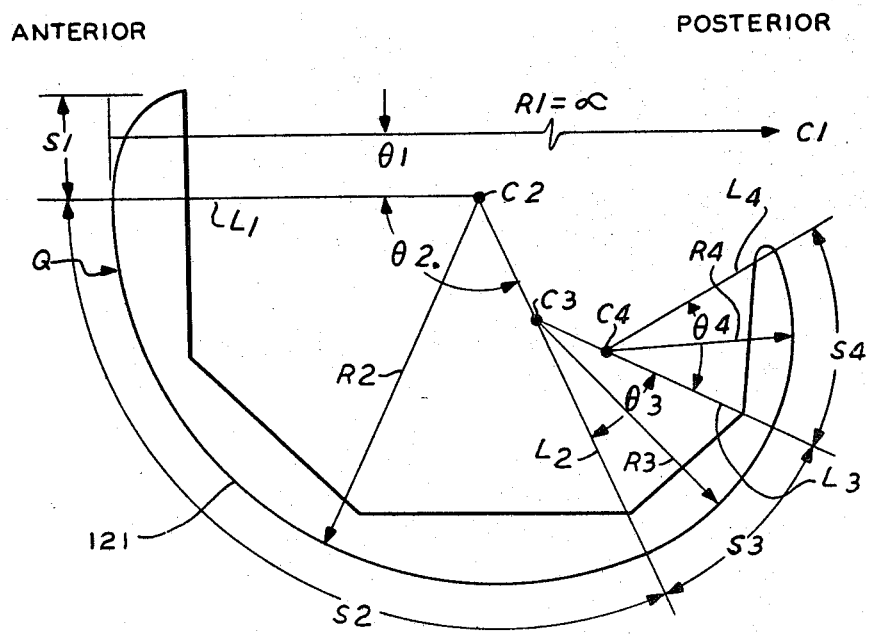
FIG. 22 illustrates the manner in which the surface of the femoral component according to the present invention is generated by a series of segments of surfaces of revolution.

Referring now to FIG. 22, it will be understood that this figure is a diagrammatic illustration showing the manner in which the series of segments of surfaces of revolution S1, S2, S3 and S4 defining the shape of the bearing surface 121 and generated and where the curve Q represents the trace of points M1 and M2 as viewed along line G (FIG. 23) resulting from the rotations about the respective generating axes generating the surface segments. It will be further understood that the shape of the bearing surface 121 is defined by a series of segments of surfaces of revolution where each pair of major generating radii D1 and D2 for generating each segment decrease in length respective as rotation of the generating curve F proceeds about each generating axis in the counterclockwise anterior to posterior direction as viewed in FIG. 22. In the present embodiment and as illustrated in FIG. 23, the pairs of major generating radii D1 and D2 are equal in each instance and may in each instance be replaced by a single major generating radius R (i.e. R1, R2, R3 and R4) as shown in FIG. 22. In this embodiment, the bearing surface 121 consists of four segments of surfaces of revolution S1, S2, S3 and S4.

S1 is generated by rotating the common generating curve F through an angle $\theta_1$ about generating axis C1 perpendicular to the plane of FIG. 22 at a major generating radius R1. In the present embodiment, R1 is equal to infinity and since only the intermediate patella bearing component 113 of FIGS. 10, 11, and 12 articulates with segment S1, it will be referred to as the patello-femoral bearing surface segment.

Segment S2 is generated by rotating the common generating curve F through an angle $\theta_2$ about generating axis C2 parallel to C1 at a major generating radius R2 where R2 is equal to radius A1 which is equal to A2 in FIG. 7; since such radii are equal, it will be understood that segment S2 has two spherical surfaces. For continuity and smoothness of bearing surface 121, axis C2 must lie on the ray L1 passing through C1 and defining the end of segment S1. This segment (S2) is of special importance since both the intermediate patella bearing component 113 and the intermediate tibial bearing component 117 articulate with this segment and since the greatest loads on these components during normal walking occur when they articulate against this femoral bearing segment. This segment (S2) will, therefore, be referred to as the primary load bearing surface segment.

Segment S3 is generated by rotating the common generating curve F through an angle $\theta_3$ about generating axis C3 parallel to C2 located at major generating radius R3 where R3 is less than R2. Again, for continuity and smoothness of bearing surface 121, axis C3 must lie on ray L2 passing through C2 and defining the end of segment S2.

Finally, segment S4 is generated by rotating the common generating curve F through an angle $\theta_4$ about generating axis C4 parallel to C2 located at major generating radius R4 which is less than R3. Again for continuity and smoothness of bearing surface 121, axis C4 must lie on ray L3 passing through C3 and defining the end of segment S3. These latter two segments will be referred to, respectively, as the first and second posterior femoral bearing surface segments.

Referring again to FIG. 8, it will be understood that FIG. 8 is a sectional view of an actual embodiment of the present invention as shown in FIG. 7 and that the segments of surfaces of revolution S1, S2, S3 and S4 shown in FIG. 22 are also shown in FIG. 8 at their respective locations.

In one embodiment of the present invention, the respective angles $\theta$ and each respective major generating radius are as follows:

| SEGMENT | $\theta$ (DEGREES) | MAJOR GENERATING RADIUS (inches) |
| --- | --- | --- |
| S1 | 0 | ∞ (displacement 0.612 inches) |
| S2 | 107.75 | 1.388 |
| S3 | 62.25 | 0.801 |
| S4 | 62 | 0.578 |

Referring again to FIGS. 8 and 22, it will be noted that the generating axes C1, C2, C3 and C4 are parallel with respect to each other and it will be understood that the tangent line G is oriented substantially parallel to the generating axes. However, in accordance with the teachings of the present invention, such need not be the case and the generating axes may be oriented other than parallel with respect to each other and, as shown in the general case illustrated in FIG. 23, the tangent line G may be oriented other than parallel to the generating axes.

Referring again to the patella prosthesis and in particular to the intermediate patella bearing component 113 of FIGS. 10, 11, and 12, it will be understood that in accordance with the further teachings of the present invention such intermediate patella bearing component 113 provides a load-bearing surface indicated by general numerical designation 125 for engaging the bearing surface 121 of femoral component 111 and which load bearing surface 125 includes a primary load bearing surface segment 126, a pair of secondary load bearing surface segments 127 and 128 and a pair of transition segments 129 and 130 between 126 and 127 and 126 and 128 respectively. Further, it will be understood in accordance with the teachings of the present invention that the shape of the load bearing surface 125 of the intermediate patella bearing component 113 is defined or generated by the common generating curve F used to generate the segments S1–S4 of the bearing surface 121 of femoral component 111. Referring to FIG. 11, it will be understood that the common generating curve F is rotated through an angle $\theta_5$ (in one embodiment angle $\theta_5$ equals 20°) about generating axis C5 at the pair of major generating radii D1 and D2 shown in FIG. 23, where D1 and D2 are each equal to major generating radius R2 shown in FIG. 22, to define the shape of the primary load bearing surface segment 126. Therefore, the patella primary load bearing surface segment 126 congruently matches the primary load bearing surface segment S2 of femoral bearing surface 121 and, upon articulating therewith, engages the primary femoral bearing surface segment S2 in sliding area contact. The secondary load bearing surface segments 127 and 128 of the patella load-bearing 125 of FIG. 11 likewise match the patella femoral bearing surface segment S1 of bearing surface 121 (in FIG. 8) and hence their shapes are defined or generated by rotating the common generating curve F about an axis C6 at infinity (and parallel to axis C5) as was done in generating the shape of segment S1 of femoral bearing surface 121. Therefore, the patella prosthesis secondary load-bearing surface segments 127 and 128 congruently match the patello-femoral bearing surface segment S1 of femoral bearing surface 121 and, upon articulating therewith, engage the femoral bearing surface segment S1 in sliding area contact. The transition segments 129 and 130 are defined by rotating the common generating curve F through an angle $\theta_6$ about axes C7 and C8 respectively at a pair of negative generating radii (directed to opposite sides of common generating curve F from those shown in FIG. 23), both about 0.30 inch in one embodiment. These transition segments 129 or 130 engage, in line contact, segments S2 and S1 of femoral bearing surface 121 near their interface as the contacts shift from segment S2 of the femoral bearing surface 121 with the primary load bearing segment 126 to contact between femoral segment S1 and the secondary load bearing segments 127 and 128.

In another embodiment of the patella prosthesis of the present invention, secondary load bearing surfaces 127 and 128 are inclined downwardly with respect to the horizontal (as viewed in FIG. 11) to better accommodate the orientation of the patella prosthesis 112 with respect to the femoral component 111 during full extension of the human knee as shown in FIG. 24 and therefore to provide a more uniform load distribution on the secondary load bearing surface segment 127 or 128.

The intermediate patella bearing component 113 is retained on the remnant of the human patella by use of the patella fixturing component 114 of FIGS. 13 and 14. Patella fixturing component 114 may be suitably affixed to the remnant human patella, using an acrylic grouting agent or cement, by crossed fixturing fins 131 and 132 on the dorsal side of the metal plate 133. Such fixturing fins resist tipping loads, as shown in FIG. 25, and, in addition, provide a reinforcing effect which allows the use of a thin metal plate 133, which is desirable, since one wishes to minimize the change in overall patella thickness resulting from prosthetic replacement so as not to adversely affect patella function, skin closure after surgery and cosmesis. The fixturing fins 131, 132 and metal plate 133 reinforce and strengthen the patella remnant and minimize the possibility of its fracture. The opposite or ventral side of metal plate 133, FIG. 13, which comprises the bulk of the secondary fixturing component bearing surface which mates with the secondary bearing surface 134 on the intermediate patella bearing component 113, is provided with a button 135 which retains intermediate patella bearing component 113 on the patella fixturing component 114 with a snap fit. As shown in FIGS. 13 and 26, the outer diameter of the button 135 is formed from a curve with two tangent radii which produce a smooth retaining male surface 136 when mated with correspondingly shaped female surface 137 (FIG. 10) provided on the intermediate patella bearing component 113. These shapes allow easy entry of the male into the female component without producing the permanent deformation characteristic of conventional snap-fit configurations. The mating conical sections provide additional secondary compressive and thrust bearing surfaces. The button 135 is provided with a generally conical shaped bearing surface 138 for rotatably engaging the correspondingly shaped conical secondary bearing surface 134 (FIG. 10) provided on the intermediate patella bearing element 118 in congruent or area rotational engagement to permit rotation of the patella with respect to femoral bearing surface 121 and the distal end of the femur about axis A8 (FIG. 27).

Further, and referring to FIG. 13, the patella fixturing component 114 is provided with a pin 139 for engaging a corresponding, curved slot 140 formed in the intermediate patella bearing component 113 (FIG. 10) to limit the relative rotation between intermediate patella bearing component 113 ad the patella fixturing component 114 and thereby prevent disorientation between the intermediate patella bearing component 113 and the femoral component 111 during implantation and subsequently during actual use. Furthermore, this limited rotation has been found to be reasonably necessary since effusion (build up of blood) post-operatively may temporarily lift the load-bearing surface 125 of the intermediate patella bearing component 113 free of the restraining effects of the femoral component 111.

It will be further noted, as shown in FIGS. 10-14, that the intermediate patella bearing component 113 and patella fixturing component 114 are made symmetrical about a plane passing through the center of the primary load bearing surface 126 and through the generating axis C5 producing primary load-bearing surface segment 126, so as to allow the use of the same patella prosthesis in either the right or the left knee. It is for this reason that two secondary load bearing segments (127 and 128) are provided on the load bearing surface 125.

Figure 28A:
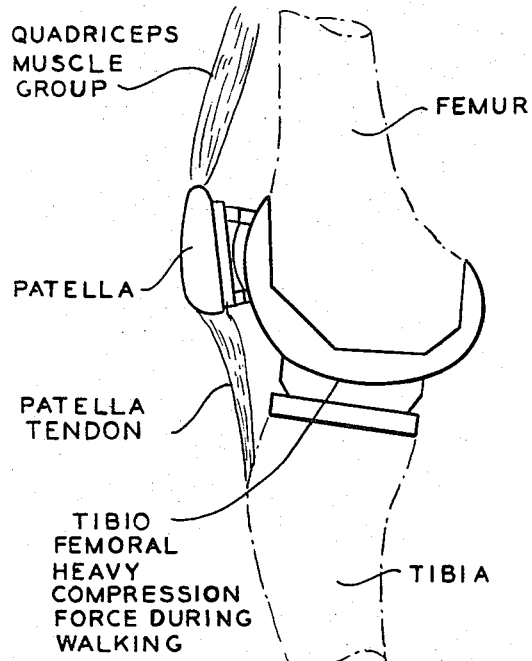
FIGS. 28A and 28B illustrate the relatively low patello-femoral compression force present at full extension of the knee.
Figure 28B:
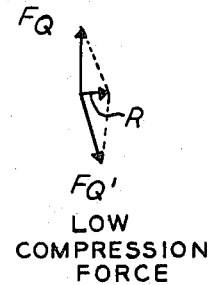

Referring now to FIGS. 28A, 28B, 29A, 29B, 30A, and 30B, there is illustrated diagrammatically the manner in which the patello-femoral portion of the tricompartmental prosthesis provides area or congruent sliding contact between the bearing surface 121 of the femoral component 111 and the load bearing surface 125 of the intermediate patella bearing component 113 over the important phases of the range of motion commonly experienced by the human knee, providing line contact between such bearing surfaces only during a brief transitional phase. Referring first to FIGS. 28A and 28B, it will be noted that at full knee extension the quadriceps muscle group provides a quadriceps force $F_Q$ which in normal activities is quite low at full extension. Because of the orientation of the force $F_Q$ the resultant patello-femoral compression force R of FIG. 28B is only a small fraction of force $F_Q$. During this phase of human knee action there is area contact between the bearing surface segments S1 and 127 (or 128) of the femoral and patella components, respectively. See FIGS. 8 and 11.

Figure 29A:
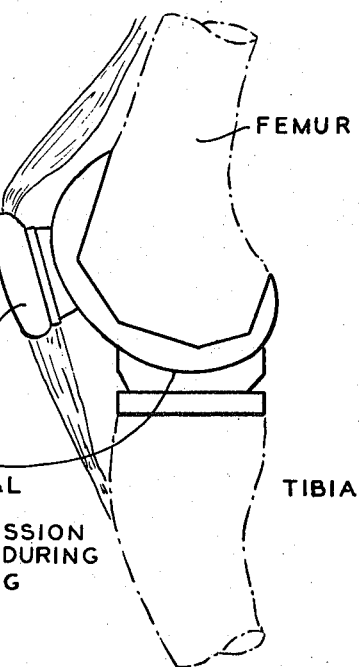
FIGS. 29A and 29B illustrate the somewhat greater patello-femoral compression force present in the load-bearing stance phase of the normal walking cycle.
Figure 29B:
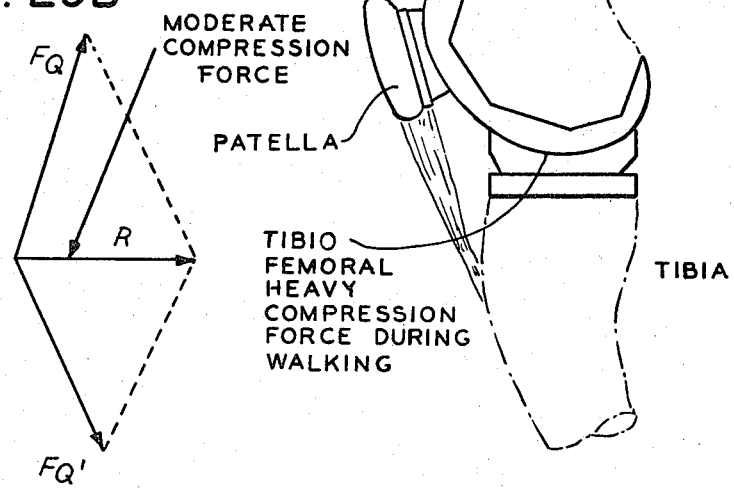

Referring now to FIGS. 29A and 29B wherein the load bearing stance phase experienced during the normal walking cycle is illustrated diagrammatically, it will be noted here the quadriceps force $F_Q$ is greater and the resultant patello-femoral compression force R is much greater than at the full extension illustrated in FIGS. 28A and 28B. This result is attributable to the greater quadriceps force $F_Q$ and the smaller included angle between the quadriceps force $F_Q$ and the patella ligament force $F'_Q$. Of course, as is known, even greater flexion angles are experienced by the human knee during stair climbing and descent and hence in these activities even greater patella bearing resultant forces R occur.

It will be understood that during the short transition phase in moving from segment S1 to segment S2 that transition segments 129 or 130 of the patella load-bearing surface 125 are in sliding line contact with the femoral bearing surface 121. As is further known, during the most common and hence most important human knee activity, namely level walking, there is no substantial quadriceps activity or force present until approximately 10° of knee flexion is achieved at which the patella articulation of the prosthesis of the present invention has just entered the primary load bearing surface segment S2 wherein there is sliding area contact between the femoral bearing surface segment S2 and the patella primary load bearing segment 126. Thus, the above-noted transitional and hence momentary line contact is not of serious concern since at this time the quadriceps force $F_Q$ is relatively small and even if it were substantial the resultant compressive force R would still be quite low because of the large included angle between forces $F_Q$ and $F_{Q'}$. Area contact is only needed during the walking load bearing and other activity phases where compression forces R are significant.

Figure 30A:
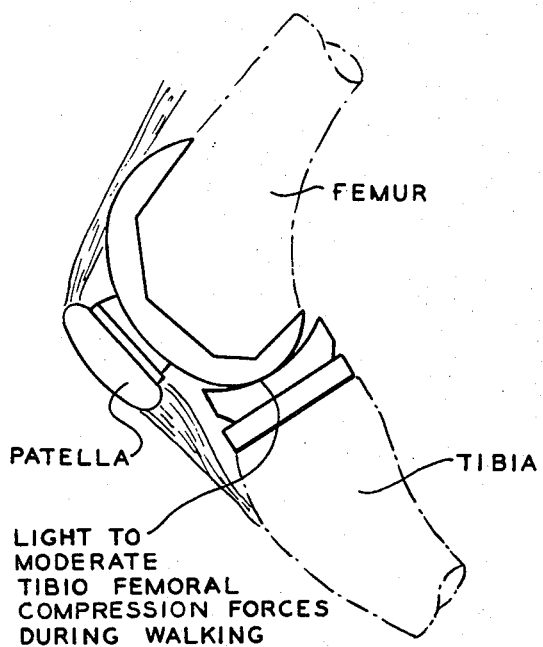
FIGS. 30A and 30B illustrate the much greater patello-femoral compression force present in deep knee flexion.

The regions S1 and S2 on the femoral component 111 and corresponding transition segments 129 or 130 and the primary and secondary load bearing surface segments 126 and 127 (or 128) are needed to produce anatomical patello-femoral articulation wherein at full extension as the superior aspect of the patella lifts off the femur as in FIG. 28A and yet allow central area contact engagement at moderate and full flexion as shown in FIGS. 29A and 30A.

Figure 30B:
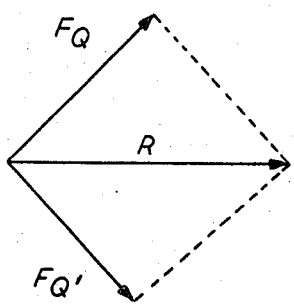

Referring now to FIGS. 30A and 30B wherein deep knee flexion is illustrated diagrammatically, it will be seen that it is during deep knee flexion that the patello-femoral compressive load R is greatest. It will be understood, and as illustrated in FIG. 30A, the patella load bearing surface 125 (FIG. 11) articulates with the same surface segment S2 (FIG. 8) wherein the tibio-femoral articulation occurs during full extension, thus, the primary load bearing surface segment S2 of bearing surface 121 supplies the femoral bearing surface for both articulations (patello-femoral and tibio-femoral articulations) at times of greatest loading during the walking gait cycle, and this commonality is a significant feature of the present invention. Of course, as is known to those familiar with the anatomy of the human knee, this situation (common articulation between a portion of the human condyles and both the patella and tibial bearing surfaces) is not present in the anatomical human knee.

Figure 31:
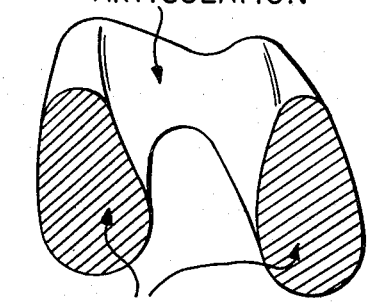
FIG. 31 is an inferior view of the distal femur, showing the femoral anterior articular cartilege involved in patello-femoral articulation, as well as the femoral posterior articular cartilege involved in tibio-femoral articulation.

As shown in FIG. 31, in the human knee the femoral anterior articular cartilege against which the human patella articulates is distinct from that which articulates with the tibia. Such natural structures adapt during development of the human knee to produce precise mating of the structural and articulation elements of the knee but such precision of mating is not practical in replacement knee prostheses because of the large individual variations found in different human knees, as well as the manufacturing and surgical difficulties involved in reproducing such precision. Thus, the use of a common femoral prosthesis primary load bearing surface segments S2 for both the patella and tibial articulations represents a significant feature in providing the needed sliding area engagement or congruency of articulation for extended wear life.

Referring again to FIG. 10, it will be noted that the depth of engagement of the patella load bearing surface 125 into the femoral bearing surface 121, distance T in FIG. 10, is substantial and hence allows substantial subluxation resistance to side thrust loads. It has been found that in individuals where this dimension is small or excessive knee valgus is present, subluxation of the patella is common. Yet in many known prior art devices, the corresponding depth of engagement is inadequate or non-existent. Further, and referring again to FIGS. 10 and 13, it will be noted that area rotatable mating fit (bearing surfaces 134 and 138) between the intermediate patella bearing component 113 and the patella fixturing component 114 allows a rotation therebetween and this rotation is highly desirable to accommodate possible surgical misalignment during implantation, as well as the small, naturally observed, patella rotation with respect to the human femur during flexion-extension movements.

Referring now to FIGS. 18, 19, 20 and 21, and to the intermediate tibial bearing component 117 shown therein, this component provides a primary load bearing surface 141 on its superior side and a second bearing surface 142 on its inferior side. The primary load bearing surface 141 is also formed as a surface of revolution and its shape is defined or generated by the common generating curve the same as or very similar to curve F used to generate the shape of segments S1–S4 of femoral bearing surface 121 and the shape of patella bearing surface 125.

Referring now to FIG. 19, it will be understood that the shape of the primary load bearing surface 141 is defined by rotating the common generating curve substantially similar to curve F through an angle $\theta 6$ (in one embodiment of the present invention $\theta 6$ equals 60 degrees) about generating axis C6 at the same major generating radii D1 and D2 shown in FIG. 23 where D1 and D2 are again each equal to R2 shown in FIG. 22. Therefore, the tibial primary load bearing surface 141 is in substantial area contact with the primary load bearing surface segment S2 of femoral bearing surface 121 and, upon articulating therewith, engages the femoral primary bearing surface segment S2 in sliding area contact. Therefore, substantially congruent articulation is provided at the tibio-femoral joint interface for approximately 36 degrees of knee flexion wherein the greatest loads during the walking cycle are experienced as indicated in FIGS. 29A and 29B.

Figure 33A:
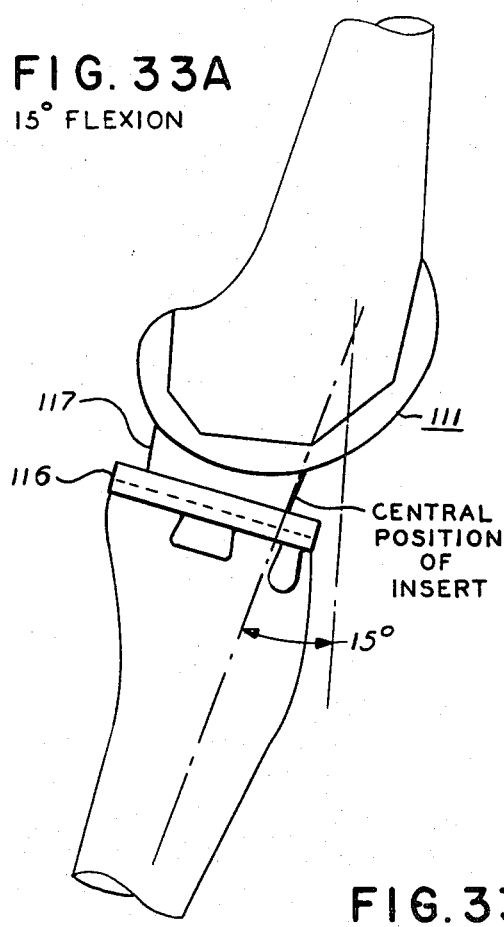
FIGS. 33A and 33B show the manner in which the intermediate tibial bearing components move posteriorly with flexion of the knee.
Figure 33B:
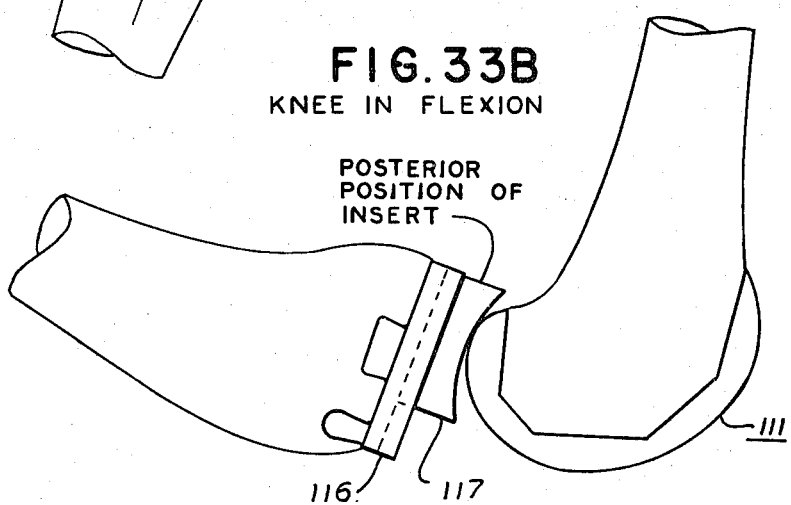

The geometry and particularly the shape of load bearing segment S2 are configured so that, in addition to producing the favorable patello-femoral and tibio-femoral articulation described, the intermediate tibial bearing components 117 are held in a forward position on the tibial platform 116, as shown in FIGS. 32A and 32B. As the knee is flexed slightly the femur, and thus the intermediate tibial bearing components 117, move rearward relative to the tibia so they then occupy a generally central position on the tibial platform 116, as shown in FIG. 33A. Additional flexure produces a small additional posterior shift of intermediate tibial bearing components 117 as a result of further anterior displacement of the tibia relative to the femur and as a result of femoral condylar geometry, as shown in FIG. 33B. This posterior shift is reduced at flexion angles above 40° by the use of small major generating radii in segments S3 and S4; shown in FIG. 8, in the New Jersey Meniscal Insert Knee Replacement. The use of smaller major generating radii in segments S3 and S4 allows full flexion without excessive shift of intermediate tibial bearing components 117, an important feature of the present invention that is not to be found in the prior-art Oxford knee.

The 0 to 90 degree flexion-extension range includes almost all strenuous activities in which an individual with an endoprosthesis is likely to engage. Articulation in the 35–95 degree range occurs in the first posterior femoral bearing segment S3 of FIG. 8 and hence there is line contact as indicated in FIG. 30A. Although such line contact or incongruency is less desirable than sliding area contact, it produces acceptably low contact stresses while allowing sufficient flexion necessary for normal activities since loads during walking in this phase of flexion are much less than in the 0–36 degree range or area contact phase. Heavy joint loading in this range of knee motion occurs much less frequently than in the 0 to 36 degree range and thus higher periodic or transitional stresses can be tolerated without producing fatigue or excessive wear. flexion from 95 degrees to 140 degrees is accommodated by the second posterior femoral bearing segment S4 of the femoral prosthesis (FIG. 8) and expected stresses at such flexion angles are such that serious permanent deformation is not anticipated except perhaps during deep knee bend exercises such as deep squats, which should of course be avoided by individuals having any knee prosthesis. Fatigue is not of concern here (segment S4) since the expected frequency of occurrence of these stresses is low. Obviously, a patient with such knees should be discouraged from performing deep knee bends or similar exercises. It should be noted that few knee prostheses allow flexion in excess of 90 degrees, and those that do, while still allowing reasonable axial rotation, experience far greater contact stress than the present invention. The last region is provided to allow the extreme flexion range which is often needed during sitting, where small loads on the knee are experienced, without producing excessive posterior shift of the intermediate tibial bearing components 117.

The two incongruent or line contact phases of contact associated with segments S3 and S4 are tolerated in order to obtain nearly normal flexion and extension motion by providing a reasonable approximation to normal condylar geometry. Incongruency in these phases occurs only in one dimension rather than two dimensions as in most prior art prostheses. Thus, normal knee motion is provided without excessive shift of intermediate tibial bearing components 117 while keeping contact stress within acceptable limits of most normal activity.

The second bearing surface 142, FIGS. 18, 19, 20, and 21, is on the inferior side of the intermediate tibial bearing component 117. This bearing surface is composed of a flat surface 143 and a projecting dovetail surface 144. The flat and dovetail bearing surfaces engage the superior surface 145 of the tibial platform component 116 shown in FIGS. 15, 16, 17, and 34, and the track surfaces 146 and 154 therein in area contact.

This tibial platform 116, as shown in FIGS. 15, 16, and 17, consists of a thick plate 147 with a notched area into which fits the section of the proximal tibia to which the cruciate ligaments are attached. Two curved tracks 148 and 153 are provided in thick plate 147. These curved tracks 148 and 153 receive and partially constrain the two identical intermediate tibial bearing components 117, which can be seen in FIGS. 32A and 32B. These bearing inserts are substantially identical to the intermediate tibial bearing component illustrated in FIGS. 18 thru 21.

The shape of the thick plate 147 of the tibial platform component 116 is contoured so as to engage, where practical, the outer cortical bone of the tibia so as to improve load bearing and to allow this component to be used for both right and left tibias. Three short spikes 149, 149, and 172 help distribute joint loads, supply additional load transfer to the cancellous bone, and provide resistance against possible tensile loading.

It will be understood that the symmetry of both intermediate tibial bearing component 117 and tibial platform component 116 eliminates the need to designate a right or left knee aspect, and thus eliminates the concern of the implanting surgeon with these matters during implantation.

Figure 35A:
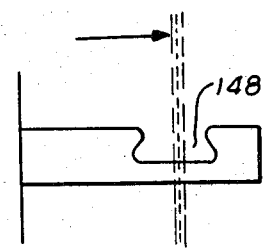
FIGS. 35A and 35B illustrate the manner in which the intermediate tibial bearing components move slightly closer together as they move forward and rearward from a central position in the curved track of the tibial platform component.
Figure 35B:
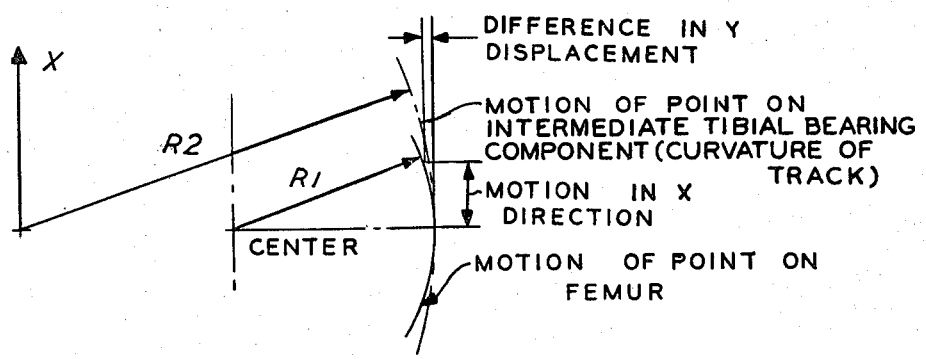
Figure 37A:
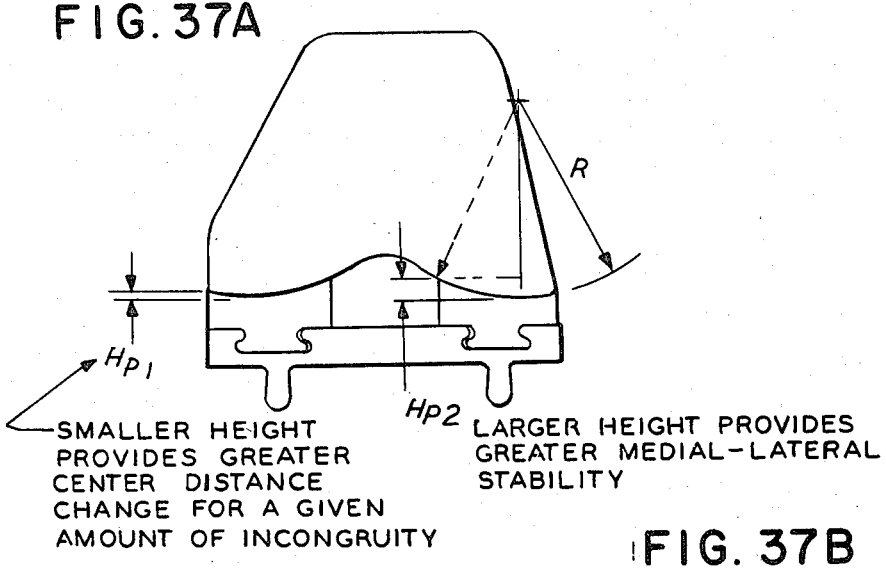
FIGS. 37A and 37B show the manner in which the use of an eccentric bearing insert (i.e. the intermediate tibial bearing component) allows a relatively great inward shift of the bearing insert with little incongruency.
Figure 37B:
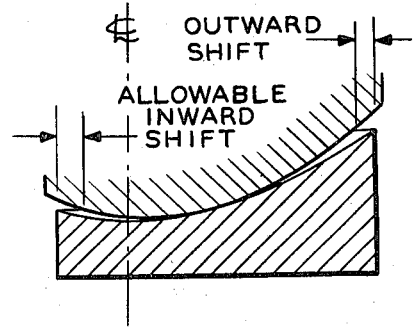

In FIG. 16, it can be seen from the shape of curved tracks 148 that as the intermediate tibial bearing components 117 move forward and rearward from the central position that they move somewhat closer together, as shown in FIGS. 35A, 35B and 36. It may be seen from FIGS. 37A and 37B that the use of an eccentric bearing insert allows a relatively great inward shift with little incongruency. For example, a total movement of ±6 mm produces a separation change of 0.5 mm. This change of separation is easily accommodated by using a very slightly incongruent surface and/or by providing a slight clearance between the walls 150 and 151 (FIG. 34) of curved tracks 148, and the mating projecting dovetail surfaces 144 of the intermediate tibial bearing component 117, shown in FIG. 19. The contact congruency ratio C, when contact is made with segment S2 of the femoral prosthesis, used in one embodiment is approximately 0.99, where C is defined as follows:

$$C = R2/R2'$$

where $R2$ = Spherical radius of primary load bearing segment S2 of bearing surface 121 on femoral component 111 (FIGS. 7,8);

and $R2'$ = Spherical radius of primary load bearing surface 141 of the intermediate tibial bearing component 117 (FIGS. 19,20).

The contact stress is thus kept quite low while still allowing the needed change in separation.

In addition to the anterior-posterior shift, axial rotation of the tibia takes place during flexion. This rotation is accommodated by the shape of the contacting surfaces, and in particular by the spherical radii of the primary load bearing segment S2 of the femoral component 111 and primary load bearing surface 141 of intermediate tibial bearing component 117, as well as by the curvature of the curved tracks 148 and 153 of tibial platform component 116. As can best be seen from FIG. 16, the center 152 of curvature of the left curved track 153 of tibial platform 116 is on a line normal to left track surface 154. This line, on which lies the center 152 of curvature of the left curved track 153, passes through the center 155 (refer to FIG. 7) of the right spherical radius of the primary load bearing segment S2 of femoral component 111 when the components are all assembled. Thus, if one were to hold the prosthesis so that it could only rotate about this normal line, the motion could be accommodated (even with perfect congruency and rigidity of the plastic) by virtue of the spherical contact on the right side and the track curvature on the left. Similarly, motion about a normal on the left side could also be accommodated. Axial motion about any other normal axis expected in the knee produces slight inward motion of the intermediate tibial bearing components 117 as shown in FIG. 36. This inward motion, as in the case where this motion is produced by anterior-posterior shift, is accommodated with the very slight incongruency used, and/or the slight clearance provided between the projecting dovetail surfaces 144 of intermediate tibial bearing components 117 and curved tracks 148 and 153 of tibial platform component 116.

The less constrained prior art Oxford knee also provides for axial rotation and anterior-posterior shift even with perfect congruency. In the present invention, such motion is obtained while allowing the utilization of stabilizing tracks.

Figure 38A:
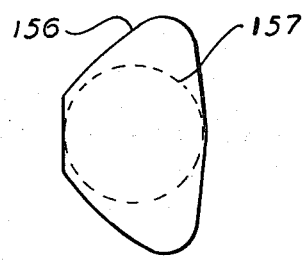
FIGS. 38A through 38C illustrate several advantages of the intermediate tibial bearing component according to the present invention. The larger platform (relative to that of the circular bearing insert of the prior-art Oxford knee) is shown in FIG. 38A.
Figure 38B:
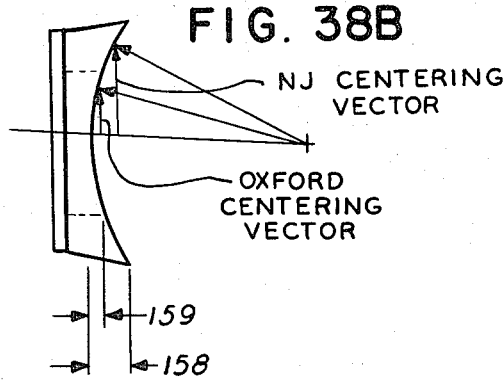

The method of track engagement utilized in the present invention has several functions:

1. It prevents rotation of the intermediate tibial bearing components 117, and thus:

(a) Allows a noncircular and larger bearing insert platform 156 (in FIG. 38A), as compared with the smaller, circular platform 157 of the prior art Oxford insert. The present invention also produces a greater dislocation height 158 as compared with the dislocation height 159 of the prior art Oxford insert as shown in FIG. 38B. This added height also allows large shifting forces for moving the bearing insert anteriorly and posteriorly against the friction generated by the large compressive load.

Figure 38C:
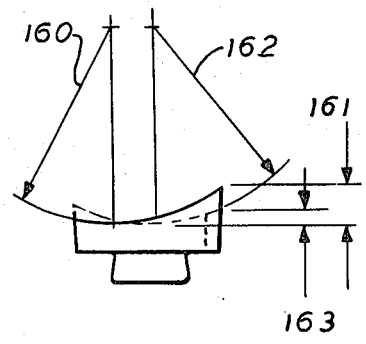

(b) Allows use of a noncentral (i.e. noncentral when viewed in the anterior-posterior direction) spherical radius 160, as can be seen from FIG. 38C, providing additional medial or lateral stability by virtue of the relatively large inside engagement height 161. This is to be contrasted with the central spherical radius 162 of the prior-art Oxford knee, with its resultant relatively small inside engagement height 163. The improved engagement of the present invention is unaffected by axial rotation or anterior-posterior shift. Such is not the case in conventional designs.

2. It provides a partially self-retaining feature for the curved tracks 148, 153. This feature, plus the longer intermediate tibial bearing components 117, eliminates the possibility of tipping and dislocation associated with the prior art prostheses discussed earlier.

3. The curved tracks 148, 153 provide thrust surfaces allowing most medial-lateral shear loads to be taken entirely by the prosthesis with no prosthesis-bone rubbing contact as in the Oxford knee.

Thus the present invention, the New Jersey Meniscal Insert Knee Replacement (NJMIK) sacrifices a small amount of congruency (and simplicity) to achieve greatly improved stability. The advantages and differences of the NJMIK compared to the prior-art Oxford knee design can be summarized as follows:

1. Use of smaller major generating radii for the posterior segments S3 and S4 (FIG. 8) of femoral component 111, thus allowing full flexion and allowing such flexion without excessive shift of the intermediate tibial bearing components 117;

2. Elimination of possible intermediate tibial bearing component dislocation modes;

3. Provision of greater insert shifting forces to overcome friction;

4. Provision of greater medial-lateral stability; and,

5. Provision of effective patello-femoral articulation coupled with tibio-femoral articulation.

The primary disadvantage of the NJMIK, which also is present in the human knee, is the loss of excellent bearing congruency beyond about 40° flexion, as previously described. It therefore seems a very advantageous tradeoff considering the limitations inherent in the prior-art Oxford knee design.

Additional benefits result from the tibial fixation methods employed.

Figure 39A:
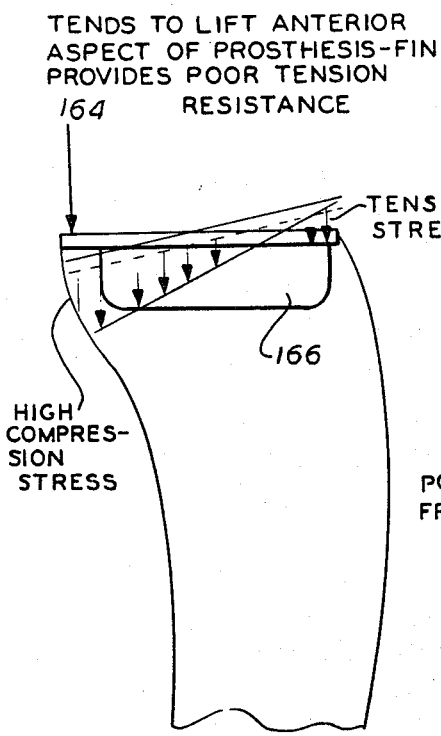
FIGS. 39A and 39B illustrate the undesirable tensile stresses produced in the prosthesis-bone interface by the MacIntosh type tibial onlays of the prior-art Oxford knee.
Figure 39B:
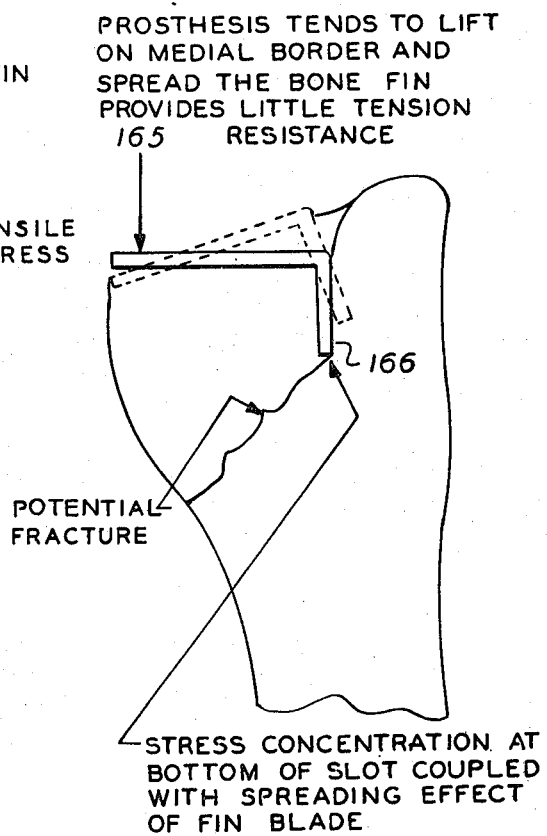

Loosening and collapse of the tibial component are major problems in knee replacement. This is true of the MacIntosh type onlays used in the prior-art Oxford knee. The problems with this type of platform are depicted in FIG. 39A, which shows posterior load 164 and lateral load 165. Note that posterior load 164 produces high compressive stress at the posterior aspect of the tibia, with tensile stress at the anterior aspect. The anterior portion of the tibial onlay tends to lift as a result of the tensile stress, as can be seen from FIG. 39A. There is also a large stress concentration effect of the fixation fin 166. The tipping of the tibial onlay also produces large posterior or lateral compressive bone stress, thereby increasing the tendency toward bone collapse as shown in FIG. 39B.

Figure 40A:
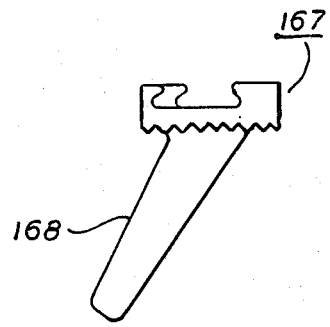
FIGS. 40A and 40B show the tibial platform of a unicompartmental version of the present invention.
Figure 40B:
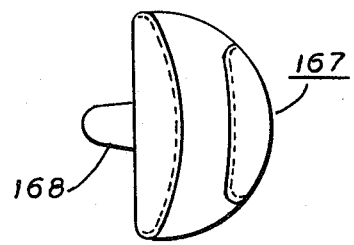
Figure 41A:
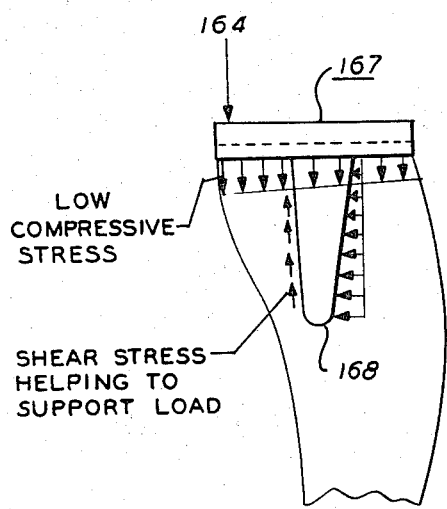
FIGS. 41A and 41B show the manner in which the spike of the tibial platform of the unicompartmental version of the present invention resists both tipping and compressive loads.
Figure 41B:
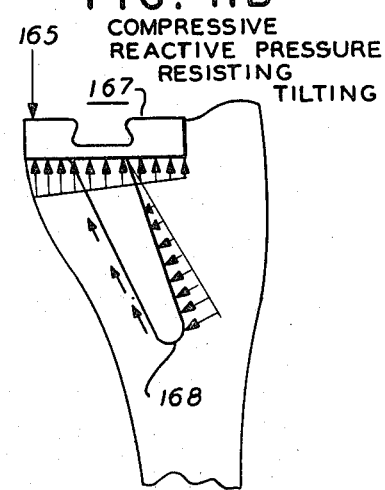

In the unicompartmental version of the present invention, tibial platform 167 of FIGS. 40A and 40B for example, tipping loads are resisted by reactive compressive loads on the spike 168. Spike 168 also helps support the direct compressive loads as well, as can be seen from FIGS. 41A and 41B. In FIGS. 41A and 41B, posterior load 164 and lateral load 165 are shown similarly to FIGS. 39A and 39B. The combined effects (tipping loads resisted by reactive compressive loads on spike 168, and direct compressive loads partially supported by spike 168) result in relatively low contact stresses on the bond, in the case of the tibial platform 167 according to the present invention.

Figure 42A:
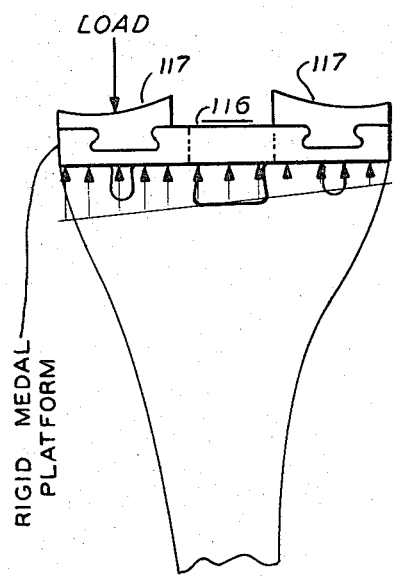
FIGS. 42A and 42B compare the tibial platform component of the present invention with a prior-art prosthesis utilizing a flexible platform, which is ineffective in producing any load-sharing across the prosthesis-bone interface.
Figure 42B:
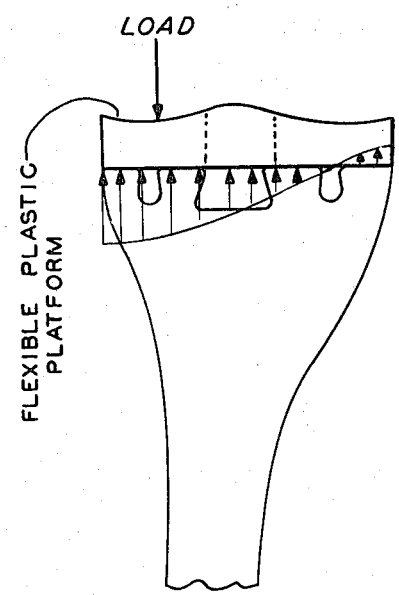

The tibial platform component 116 according to the present invention resists tipping forces by means of a bridge 169, which can be seen in FIG. 16. Bridge 169 connects the two tibial plateau sections 170 and 171, and transfers some of the load from one plateau section to the other, as can be seen from FIG. 42A. Shown for comparison in FIG. 42B is a prior-art prosthesis with a flexible platform, which is ineffective in producing any load-sharing across the prosthesis-bone interface. Also, the short anterior spike 172 of the present invention, shown in FIGS. 15 and 17, serves to resist posterior loads. Furthermore, bridge 169 inhibits the outward splaying fracture of the tibial condyles depicted in FIG. 39B.

It will be further understood by those skilled in the art and referring again to the femoral component 111 and the patella prosthesis 112, that the bearing surfaces 173 and 138 of the patella fixturing component 114 (FIG. 13) and bearing surfaces 137 and 134 of the intermediate patella component 113 (FIG. 10) accommodate both axial surgical misalignment and normal rotation while permitting area contact between the bearing segments S1 and S2 of the femoral component 111 and the load-bearing surface 125 of the intermediate patella bearing component 113. Similarly, it will be further understood that the bearing surfaces 143 and 144, respectively, of the intermediate bearing components 117 (FIGS. 18–21) and the mating bearing surfaces of the tibial platform component 116 accommodate both axial surgical misalignment and normal rotation while permitting sliding substantially area contact between the primary load bearing segment S2 of femoral component 111 and the primary load bearing surface 141 of the intermediate tibial bearing component 117. This substantial congruence is provided in the important stance phase of walking illustrated diagrammatically in FIG. 29A.

Figure 47A:
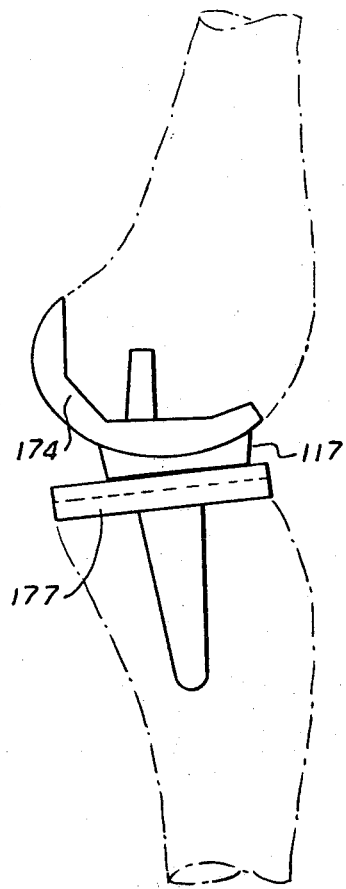
FIGS. 47A and 47B show an implanted unicompartmental version of the present invention.
Figure 47B:
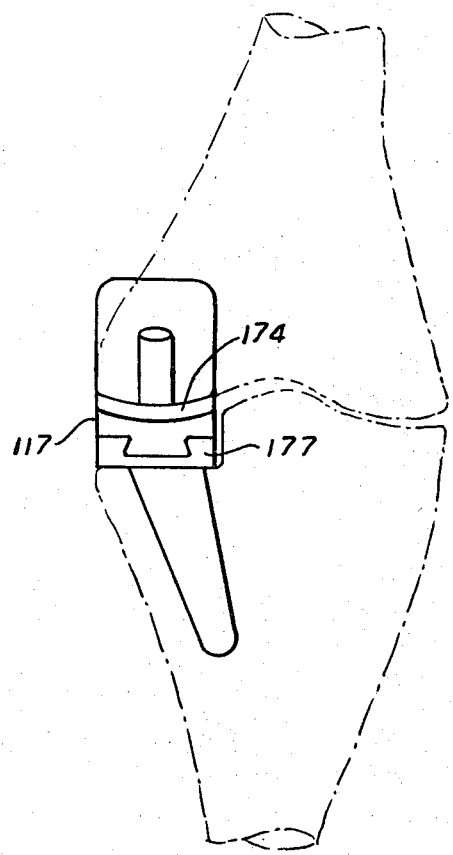
Figure 43:
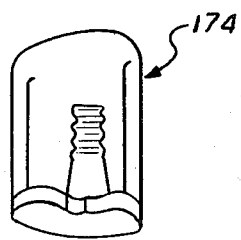
FIGS. 43 and 44 show the femoral component of a unicompartmental version of the present invention.
Figure 44:
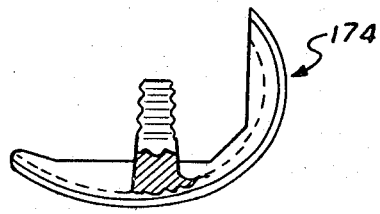

Referring now to FIGS. 43–46, there is shown a bicompartmental embodiment of the present invention which utilizes a pair of individual femoral components 174 and 175 and, as illustrated diagrammatically in FIGS. 45 and 46, omits the use of the patella prosthesis 112. Referring specifically to FIGS. 43 and 44, there is shown a right individual femoral component 174 and it will be understood that the individual femoral component 175 shown in FIGS. 45 and 46 is the mirror image of the right femoral component 174 shown in FIGS. 43 and 44. Tibial prosthesis 115 of this embodiment is the same as the tibial prosthesis 115 already described. It will be understood, and referring to FIG. 46, that the individual femoral components, e.g. 175, are provided with a load bearing surface 176 which is identical to the segments S4, S3, and a major portion of the primary load bearing segment S2 shown in FIG. 8. Thus, it will be further understood that segment S2 of these individual femoral components 174 and 175 are in area contact with the primary load bearing surface 141 of the intermediate tibial bearing component 117 as taught above, thus providing the same tibio-femoral articulation as described above. For unicompartmental replacement a tibial platform 177, as shown in FIGS. 47A and 47B, is used together with an intermediate tibial bearing component 117, as shown in FIGS. 18–21. FIGS. 47A and 47B show the assembly of tibial platform 177 and intermediate tibial bearing component 117 to form a unicompartmental knee replacement.

Referring again to FIGS. 18–21, it will be still further understood by those skilled in the art that the intermediate tibial bearing component 117 may be easily removed intraoperatively to allow replacement of this component with an intermediate tibial bearing component having a thickness providing proper ligamentous (collateral ligaments) tension.

Thus, a number of intermediate tibial bearing components of varying thicknesses may be provided so that the implanting surgeon may shim for proper ligamentous tension or for valgus angle without disturbing fixtured components, e.g. tibial platform component 116 and femoral component 111. Further, such structure allows easy replacement of the intermediate tibial bearing component 117 in the event of unusual or unexpected wear or deformation. Similarly, this is true with respect to the patella prosthesis 112 wherein the intermediate patella bearing component 113 may be of varying thicknesses and replaceable in the event of unusual or unexpected wear or deformation.

It will be further understood that the femoral component 111, the patella fixturing component 114, and the tibial platform component 116 may be made preferably of a surgical metal such as cobalt-chromium alloy or titanium or stainless steel but may be made of any relatively rigid material (compared with the grouting agent) that is biocompatible, capable of withstanding the applied loads, and possesses adequate bearing properties against the intermediate bearing inserts, e.g. the intermediate patella bearing component 113 and intermediate tibial bearing component 117 may be made of any biocompatible material strong enough to withstand loads and adequate in bearing against the material with which it is engaged. Preferably these components are made of a plastic, such as ultra-high molecular weight polyethylene or copolymer acetal.

A prosthetic ankle, an alternate embodiment of the present invention, is shown in FIGS. 48, 49, and 50. Talar platform component 178 is implanted in the talus, and tibial component 179 is implanted in the distal tibia. Intermediate bearing component 180 is interposed between talar platform component 178 and tibial component 179. Talar platform component 178 has a superior bearing surface 181, seen in FIG. 48, which consists of a segment of a surface of revolution produced by a generating curve, as can be seen in FIGS. 48 and 50. The generating curve, in this case, may typically consist of two 0.625 inch radius circular arcs connected by two 20° tangent lines to a 0.250 inch radius circular arc. This arrangement is similar in form to the generating curve used for the knee embodiment previously described.

The inferior portion of talar platform component 178 includes a fixation fin 182, seen in FIG. 48, with serrated sides for implantation into the talus. Tibial component 179 consists of a flat plate 183 with serrated top edge 184 and a fixation fin 185, both of which are used for implantation into the tibia. The plastic intermediate bearing component 180 has an inferior bearing surface 186 complementary to the superior bearing surface 181 of talar platform component 178. Intermediate bearing component 180 is also provided with a flat superior bearing surface 187 which matches flat inferior bearing surface 188 of tibial component 179.

It is important to recognize that the superior bearing surface 181 of talar platform component 178, by virtue of its shape, acts as a track to constrain the motion of intermediate bearing component 180.

The ankle prosthesis illustrated in FIGS. 48–50 provides flexion-extension motion by rotation of the talar platform component 178 relative to the intermediate bearing component 180. There is sliding engagement of the inferior bearing surface 186 of intermediate bearing component 180 with the superior bearing surface 181 of talar platform component 178 as the ankle is flexed or extended, thereby providing flexion-extension motion between the tibia and the talus.

Sliding engagement of the flat superior bearing surface 187 of intermediate bearing component 180 with the flat inferior bearing surface 188 of tibial component 179 allows anterior-posterior translation as well as limited medial-lateral translation. The medial-lateral translation is constrained by anatomical features, namely the maleali of the ankle. The anterior-posterior motion is constrained by the action of the ligaments. Thus, the prosthesis of FIGS. 48–50 includes no mechanical constraints against anterior-posterior or medial-lateral translation, a desirable feature because it minimizes force loads on the components of the prosthesis.

The prosthetic joint of FIGS. 48–50 also allows axial rotation, that is, rotation about the axis of the femur, without any restraint other than that provided by natural tissues. In addition, it provides unrestrained flexion-extension. The purpose of the track (i.e. the characteristic shape of the generating curve used for the superior bearing surface 181 of talar platform component 178) is to retain the intermediate bearing component so as to prevent its moving outside the medial-lateral borders of talar platform component 178. In this way intermediate bearing component 180 is prevented from impinging upon adjacent bone.

The prosthetic joint of FIGS. 48–50 differs from one-half of the prior-art Oxford knee by virtue of the track-type of contact between talar platform component 178 and intermediate bearing component 180, and also because it affords flexion-extension motion without the possibility of eversion-inversion, at least so long as the joint is under compressive force loads (the normal situation). Axial rotation only is provided by the sliding engagement of the flat superior bearing surface 187 of intermediate bearing component 180 with the flat inferior bearing surface 188 of tibial component 179. The prior-art Oxford knee, on the other hand, incorporates a spherical bearing arrangement allowing three degrees of freedom of rotational motion, rather than two, as provided by the ankle prosthesis according to the present invention.

Figure 51:
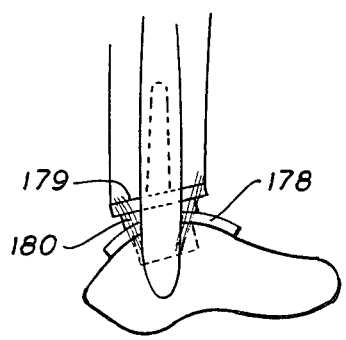
FIGS. 51 and 52 show the implanted ankle prosthesis according to the present invention.
Figure 52:
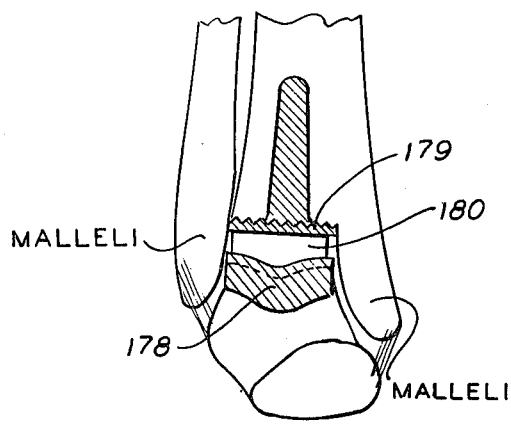
Figure 53:
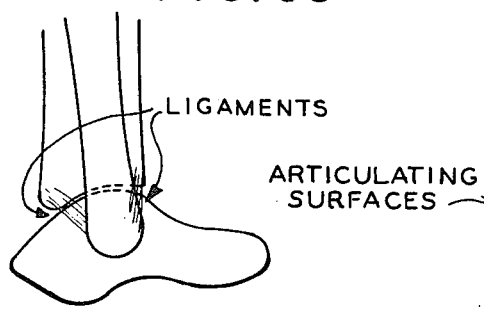
FIGS. 53 and 54 show an anatomical ankle, for comparison with the implanted ankle prosthesis of FIGS. 51 and 52.
Figure 54:
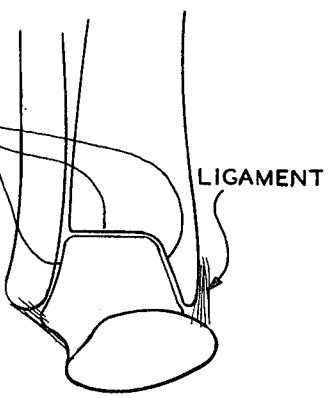

An implanted prosthetic ankle is shown in FIGS. 51 and 52. Visible in FIGS. 51 and 52 are talar platform component 178, intermediate bearing component 180, and tibial component 179. For comparison, an anatomical ankle is illustrated in FIGS. 53 and 54.

Figure 55:
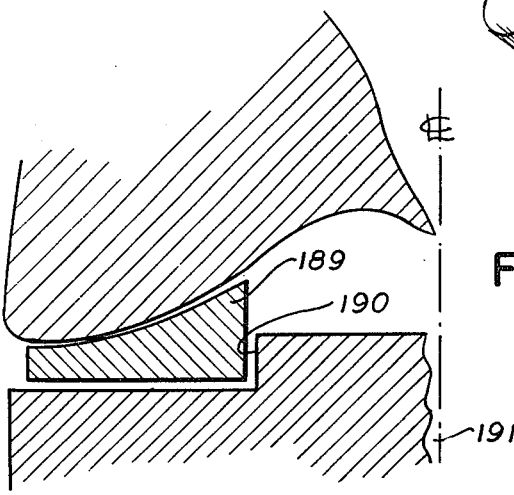
FIG. 55 shows, in schematic cross-section, an alternative track (consisting of just a shoulder, rather than a channel) suitable for applications where force loads applied to the prosthetic joint are such as to insure retention of the bearing insert against the shoulder.

It will be recognized that the track of the present invention, which serves to constrain motion of a bearing insert, can take many forms. For example, there is the track with retention, shown in cross-section in FIG. 34, and there is the track of the ankle prosthesis of FIG. 48. FIG. 55 illustrates, in cross-section, still another type of track, suitable for applications where force loads applied to the prosthetic joint are such as to insure retention of bearing insert 189 against shoulder 190 of platform component 191.

SURGICAL IMPLANTATION PROCEDURE FOR KNEE ENDOPROSTHESIS

The patient is placed in a supine position on the operating table. The knee is prepped and draped in a sterile fashion. A thigh tourniquet previously applied is inflated to 400 mm Hg after elevation of the leg for one minute to allow for venous run-off.

The knee is fully extended and a gently curved S-shaped incision is made on the tibial tubercle up towards the medial border of the patella tendon, then curving posteriorly along the medial border of the vastus medialis.

The medial retinaculum, capsule and synovial layer are incised in line with the skin incision. The vastus medialis muscle belly is elevated free from its attachment to the adductor magnus tendon. The patella is reflected laterally exposing the entire tibio-femoral joint. If there is excessive tension in the quadriceps mechanism preventing complete lateral displacement of the patella, then sharp detachment of the medial ¼ of the patella tendon from the tibial tubercle may be necessary. In a similar fashion, further blunt disection of the medial attachment of the vastus medialis may be needed to mobilize the quadriceps mechanism proximally. These maneuvers will allow complete flexion of the knee to 110 degrees with complete anterior exposure of the joint.

At this time, excision of hypertrophic synovium and redundant fat pad is performed. Medial and lateral menisectomy will facilitate exposure of the tibial plateau borders and should be performed. Examination of the intercondyler contents will reveal the condition of the cruciates. Redundant synovium should be excised from this region to prevent possible impingement or overgrowth onto the tibial component surface With the proximal tibial and distal femur cleared of soft tissue debris, bone guards are slid posteriorly between the collateral ligaments and the posterior capsule to protect the posterior neurovascular bundle during resection of the articular surfaces. A ¾" periosteal elevator may be used to develop the soft tissue planes for the bone guards, which also serve as knee retractors.

The knee is flexed to 100 degrees and a drill hole at the intercondyler notch border is made with a ¼" drill. The drill is taken down to the level of the posterior femoral shaft. Next, a tibial resection jig is placed with a spike located on the posterior aspect of the femoral shaft and a distal limb of the instrument parallel to the tibia. With the collateral ligaments in tension during this flexion phase, a proper resection plane is insured by use of the parallel cutting slots available in the jig. The jig has an automatic 10 degree retroversion angle insured when the knee is flexed parallel to the distal limb of the jig. Using an oscillating saw, the tibial preparation is made leaving a ridge of bone to which the cruciate ligaments insert. The resection planes are made at 5, 10, or 15 mm, depending upon the amount of bone stock available for perpendicular loading of the tibial component. Once the proper flexion tension has been achieved and the bone resection has been made, the tibial alignment jig is removed from the femoral shaft and the femoral shaper is next replaced into the same channel. The femoral shaper is situated such that the anterior and posterior cuts are symmetrically parallel to the femoral condyles. Using again an oscillating saw in these cuts, the anterior surface and posterior condyles of the femur are resected. The knee is then brought into full extension after removal of the femoral shaper and an extension femoral alignment jig is placed into the joint. With manual traction on the femur and aligning an adjustable valgus guide into 5 to 10 degrees of physiologic valgus, the horizontal cut on the distal femur is made to insure adequate extension tension of the collateral ligaments.

Once this cut has been made using the oscillating saw, the extension alignment jig is removed from the knee joint. The knee is again flexed and an oblique osteotomy jig is replaced into the fixturing hole and using a mallet impacted into the distal femoral bone stock. The anterior and posterior oblique cuts are then made in line with the jig surface and a central notch of the oblique osteotomy jig is used to trim away the boney surface for the anterior femoral flange. The oblique osteotomy jig is removed and the alignment holes made by the jig are curetted out to accept the fixturing pins of the femoral prosthesis. A trial fit of the femoral component is next made. Excessive bone stock is trimmed to insure proper contact of all surfaces. Next, the tibial preparation is completed. A marking template is used to mark out the tibial component spike positions. Following marking with methylene blue, tibial component spike channels are fashioned using a curette or gouge. A trial seating of the tibial component is next made and proper bone resection is performed at this time to insure excellent metal to bone contact of the prosthesis. With resections of both bones now finished, the trial reduction of the tibial and femoral components is made as follows:

The metal tibial component is placed on the proximal tibia and the appropriate intermediate bearing components are inserted into place. Next, the femoral component is placed in its proper position and the knee joint is tested in both flexion and extension for proper ligamentous tension. If resection cuts have been made properly, there should be no gross instability. Should mild laxity exist in flexion and extension, then thicker intermediate tibial bearing components may be used to tighten the collateral ligaments. The bearing heights come in 2.5 mm increments and may be used to finely adjust the ligamentous tension at this stage. These may also be used to correct varus-valus alignment. Once the tibial-femoral resections have been properly prepared, attention is given to the patella replacement. Using a scalpel, the synovial tissue and retinaculum are freed from the periphery of the patella down to the level of the patella tendon. A reciprocating saw is then used to remove the articular surface. The plane of the cut should parallel the inferior surface of the patella tendon.

A patella marking template is now centered over the horizontal and vertical axis of the patella with the long fixturing fin directed toward the lateral aspect. Methylene blue dye is used to mark the fin channels for the fixturing fins of the component. These channels are taken to a depth of ¼" and undercut for mechanical locking of the cement.

The trial patella replacement can now be seated to assess the fit. Any boney impingement is removed to insure proper seating. The patella is reflected to its anatomical position to check the alignment in the femoral track. A range of motion may now be tested with all three components in place. The patella prosthesis should center in the femoral track and easily glide along the femoral flange without binding. Restricting adhesions or boney impingement should be completely corrected at this time.

The components are removed after a satisfactory trial fit and the wound is thoroughly irrigated with antibiotic saline solution. The first batch of methylmethacrylate is mixed and placed on the tibial surface with the knee in the flexed position. The tibial component is gently slid into its fixturing channels and firmly held in compression until complete polymerization has been obtained. During the setting phase, excess methylmethacrylate may be trimmed using a scalpel and curette from the edges of the tibial component. Next, the bearing components are placed into the tibial component and the femoral component is cemented in place. Excess methylmethacrylate is removed from around the femoral component to insure that the bearing surface will remain free of this abrasive agent. With a third batch of methylmethacrylate, or else using a portion of that cement used for the femoral component, the cancellous patella bed is covered. The patellar component fixturing fins are firmly pressed into their mating channels and the component is held tightly with a patellar component clamp. Excess methylmethacrylate may now be removed from the edges of the patella backplate. Upon complete polymerization of all cement beds, a range of motion is again tested after returning the patella to its anatomical position. Two medium sized hemovac drains are now placed in the joint space and brought to exit laterally above the incision line. A single layer closure of capsule and retinaculum is performed with #2-0 chromic suture with the knee flexed 30 degrees for the first several sutures, then to 60 degrees with the second set of sutures, and finally, to 90 degrees for the remaining closure sutures. Subcutaneous tissue is closed with #3-0 plain suture, skin in re-approximated in a tension-free fashion with #3-0 nylon suture. Hemovac drains are hooked to suction and a Robert-Jones compression dressing is applied. The leg is elevated and the patient is taken to the recovery room where ice packs are placed about the knee.

It will be understood by those skilled in the art that many modifications and variations of the present invention may be made without departing from the spirit and the scope thereof.

What is claimed is:

1. An improved prosthetic knee joint for implantation in the knee of the type including:
   (a) tibial platform means having a first superior bearing surface at least a portion of which has no substantial curvature in the anterior-posterior direction, the tibial platform means for replacing tibial portions of a knee;
   (b) bearing insert means having a first inferior bearing surface for slidably engaging at least the portion of the first superior bearing surface of the tibial platform means which has no substantial curvature in the anterior-posterior direction, the bearing insert means having a second superior bearing surface, the bearing insert means for providing an articulated joint between the tibial platform means and a femoral component means;
   (c) femoral component means having a second inferior bearing surface for slidably engaging the second superior bearing surface of the bearing insert means, the femoral component means for replacing femoral portions of the knee;
   wherein the improvement comprises
   (d) the bearing insert means experiencing anterior-posterior shift relative to at least the portion of the first superior bearing surface of the tibial platform means which has no substantial curvature in the anterior-posterior direction during flexion and extension of the knee; and
   wherein the improvement comprises:
   (e) the second inferior bearing surface of the femoral component means comprising a plurality of surface segments defined by rotating a common plane generating curve about a plurality of parallel axes of rotation whereby the second inferior bearing surface of the femoral component upon slidably engaging the second superior bearing surface of the bearing insert means facilitates control of the anterior-posterior shift of the bearing insert means relative to at least the portion of the first superior bearing surface of the tibial platform means which has no substantial curvature in the anterior-posterior direction during flexion and extension of the knee.

2. An improved prosthetic joint as recited in claim 1, wherein;
   (a) the second inferior bearing surface of the femoral component means comprises a first surface segment defined by rotating the common plane generating curve about a first axis;
   (b) the second inferior bearing surface of the femoral component means also comprises a second surface segment defined by rotating the common plane generating curve about a second axis;
   (c) wherein the first surface segment and the second surface segment adjoin to form an intersection; and,
   (d) wherein the second axis lies in a plane containing the first axis and a point on the intersection producing a smooth continuous bearing surface.

3. An improved prosthetic joint as recited in claim 1, wherein:
   (a) a radius of curvature, defined by a distance from a given point on the common plane generating curve to successive axes of the plurality of parallel axes of rotation, is monotonically decreasing for surface segments ranging from anterior to posterior;
   (b) whereby full flexion of the prosthetic joint is facilitated.

4. An improved prosthetic joint for implantation in an anatomical joint and of the type including:
   (a) platform means having a first bearing surface at least a portion of which has no substantial curvature in a predetermined direction, the platform means for being secured to a first bone of an anatomical joint;
   (b) bearing insert means having a second bearing surface for slidably engaging at least the portion of the first bearing surface of the platform means which has no substantial curvature in the predetermined direction, the bearing insert means having a third bearing surface, the bearing insert means for providing an articulated joint between the platform means and a second bone component means;
   (c) second bone component means having a fourth bearing surface for slidably engaging the third bearing surface of the bearing insert means, the second bone component means for being secured to a second bone of the anatomical joint;
   (d) the bearing insert means experiencing sliding movement relative to at least the portion of the first bearing surface of the platform means which has no substantial curvature in the predetermined direction during articulation of the joint; and
   wherein the improvement comprises:
   (e) the fourth bearing surface of the second bone component means comprising a plurality of surface segments defined by rotating a common plane generating curve about a plurality of parallel axes of rotation whereby the fourth bearing surface of the second bone component means upon slidably engaging the third bearing surface of the bearing insert means facilitates control of the movement of the bearing insert means relative to at least the portion of the first bearing surface of the platform means which has no substantial curvature in the predetermined direction during articulation of the joint.

5. An improved prosthetic joint as recited in claim 4, wherein:
(a) the fourth bearing surface of the second bone component means comprises a first surface segment defined by rotating the common plane generating curve about a first axis;
(b) the fourth bearing surface of the second bone component means also comprises a second surface segment defined by rotating the common plane generating curve about a second axis;
(c) wherein the first surface segment and second surface segment adjoin to form an intersection; and,
(d) wherein the second axis lies in a plane containing the first axis and a point on the intersection producing a smooth continuous bearing surface.

6. An improved prosthetic joint as recited in claim 4, wherein:
(a) a radius of curvature, defined as a distance from a given point on the common plane generating curve to successive axes of the plurality of parallel axes of rotation, is monotonically decreasing for surface segments ranging from anterior to posterior;
(b) whereby full flexion of the prosthetic joint is facilitated.

* * * * *